US011422125B2

(12) United States Patent
Klimanskaya et al.

(10) Patent No.: US 11,422,125 B2
(45) Date of Patent: Aug. 23, 2022

(54) ASSAYS FOR POTENCY OF HUMAN RETINAL PIGMENT EPITHELIUM (RPE) CELLS AND PHOTORECEPTOR PROGENITORS

(71) Applicant: Astellas Institute for Regenerative Medicine, Westborough, MA (US)

(72) Inventors: Irina V. Klimanskaya, Upton, MA (US); Julie Kathryn Carson, Acton, MA (US); Roger Gay, Acton, MA (US); Yordanka Gikova Ivanova, Sturbridge, MA (US)

(73) Assignee: Astellas Institute for Regenerative Medicine, Westborough, MA (US)

( * ) Notice: Subject to any disclaimer, the term of this patent is extended or adjusted under 35 U.S.C. 154(b) by 325 days.

(21) Appl. No.: 15/560,584

(22) PCT Filed: Mar. 23, 2016

(86) PCT No.: PCT/US2016/023839
§ 371 (c)(1),
(2) Date: Sep. 22, 2017

(87) PCT Pub. No.: WO2016/154357
PCT Pub. Date: Sep. 29, 2016

(65) Prior Publication Data
US 2018/0052150 A1    Feb. 22, 2018

Related U.S. Application Data

(60) Provisional application No. 62/136,660, filed on Mar. 23, 2015.

(51) Int. Cl.
G01N 33/50    (2006.01)
G01N 33/58    (2006.01)
G01N 33/84    (2006.01)

(52) U.S. Cl.
CPC ....... *G01N 33/5005* (2013.01); *G01N 33/582* (2013.01); *G01N 33/84* (2013.01); *G01N 2800/164* (2013.01)

(58) Field of Classification Search
CPC .. G01N 33/5005; G01N 33/84; G01N 33/582; G01N 2800/164
See application file for complete search history.

(56) References Cited

U.S. PATENT DOCUMENTS 6,432,711 B1    8/2002    Dinsmore et al.
7,736,896 B2    6/2010    Klimanskaya et al.
(Continued)

FOREIGN PATENT DOCUMENTS

JP    2014-533289 A    12/2014
WO    WO 1995/012665 A1    5/1995
(Continued)

OTHER PUBLICATIONS

International Search Report and Written Opinion dated Jun. 10, 2016 for Application No. PCT/US2016/023839.
(Continued)

*Primary Examiner* — Samuel P Siefke
(74) *Attorney, Agent, or Firm* — Wolf, Greenfield & Sacks, P.C.

(57) ABSTRACT

This disclosure provides a new phagocytosis assay to test the function of RPE cells and photoreceptor progenitors using a pH sensitive fluorescent label.

22 Claims, 6 Drawing Sheets

(56) References Cited

U.S. PATENT DOCUMENTS

| | | |
|---|---|---|
| 7,794,704 B2 | 9/2010 | Klimanskaya et al. |
| 7,795,025 B2 | 9/2010 | Klimanskaya et al. |
| 7,838,727 B2 | 11/2010 | Lanza et al. |
| 7,893,315 B2 | 2/2011 | Chung et al. |
| 7,910,369 B2 | 3/2011 | West et al. |
| 8,268,303 B2 | 9/2012 | Klimanskaya et al. |
| 8,597,944 B2 | 12/2013 | West et al. |
| 8,642,328 B2 | 2/2014 | Lanza et al. |
| 8,742,200 B2 | 6/2014 | Chung et al. |
| 8,796,021 B2 | 8/2014 | Lanza et al. |
| 8,889,122 B2 | 11/2014 | Dinsmore |
| 8,961,956 B2 | 2/2015 | Kimbrel et al. |
| 8,962,321 B2 | 2/2015 | Kimbrel et al. |
| 9,040,038 B2 | 5/2015 | Klimanskaya et al. |
| 9,040,039 B2 | 5/2015 | Klimanskaya et al. |
| 9,040,770 B2 | 5/2015 | Klimanskaya et al. |
| 9,045,732 B2 | 6/2015 | Klimanskaya et al. |
| 9,080,150 B2 | 7/2015 | Klimanskaya et al. |
| 9,181,524 B2 | 11/2015 | Klimanskaya et al. |
| 9,193,950 B2 | 11/2015 | Klimanskaya et al. |
| 9,550,974 B2 | 1/2017 | Lanza et al. |
| 9,562,217 B2 | 2/2017 | Klimanskaya et al. |
| 9,617,512 B2 | 4/2017 | Chung et al. |
| 9,649,340 B2 | 5/2017 | Klimanskaya et al. |
| 9,650,607 B2 | 5/2017 | Klimanskaya et al. |
| 9,730,962 B2 | 8/2017 | Klimanskaya et al. |
| 9,752,118 B2 | 9/2017 | McCabe et al. |
| 9,763,984 B2 | 9/2017 | Feng et al. |
| 9,993,503 B2 | 6/2018 | Feng et al. |
| 10,072,243 B2 | 9/2018 | Chung et al. |
| 10,077,424 B2 | 9/2018 | Malcuit et al. |
| 10,307,444 B2 | 6/2019 | Lanza et al. |
| 10,426,799 B2 | 10/2019 | Feng et al. |
| 10,485,829 B2 | 11/2019 | Malcuit et al. |
| 10,501,723 B2 | 12/2019 | West et al. |
| 10,584,313 B2 | 3/2020 | Lanza et al. |
| 10,894,065 B2 | 1/2021 | Feng et al. |
| 11,013,808 B2 | 5/2021 | Gay et al. |
| 11,241,460 B2 | 2/2022 | Lanza et al. |
| 2002/0001842 A1 | 1/2002 | Chapman |
| 2002/0132346 A1 | 9/2002 | Cibelli |
| 2002/0187550 A1 | 12/2002 | Dinsmore |
| 2003/0213008 A1 | 11/2003 | Perry et al. |
| 2003/0224345 A1 | 12/2003 | West et al. |
| 2004/0146865 A1 | 7/2004 | Robl et al. |
| 2004/0180430 A1 | 9/2004 | West et al. |
| 2004/0199935 A1 | 10/2004 | Chapman |
| 2005/0025750 A1 | 2/2005 | Fissore et al. |
| 2005/0255596 A1 | 11/2005 | West et al. |
| 2006/0018886 A1 | 1/2006 | Klimanskaya et al. |
| 2006/0031944 A1 | 2/2006 | Dinsmore et al. |
| 2006/0031951 A1 | 2/2006 | Klimanskaya |
| 2006/0031955 A1 | 2/2006 | West et al. |
| 2006/0112438 A1 | 5/2006 | West et al. |
| 2006/0206953 A1 | 9/2006 | Lanza et al. |
| 2006/0240556 A1 | 10/2006 | Cibelli |
| 2006/0263338 A1 | 11/2006 | Jacoby et al. |
| 2006/0276685 A1 | 12/2006 | Dinsmore |
| 2007/0031386 A1 | 2/2007 | Klimanskaya |
| 2007/0067860 A1 | 3/2007 | West et al. |
| 2008/0057041 A1 | 3/2008 | Chung et al. |
| 2008/0085517 A1 | 4/2008 | Robl et al. |
| 2008/0206863 A1 | 8/2008 | Dinsmore et al. |
| 2009/0126032 A1 | 5/2009 | Perry et al. |
| 2009/0253201 A1 | 10/2009 | Dinsmore et al. |
| 2009/0271335 A1 | 10/2009 | West et al. |
| 2010/0167404 A1 | 7/2010 | West et al. |
| 2010/0240132 A1 | 9/2010 | Lanza et al. |
| 2010/0299765 A1 | 11/2010 | Klimanskaya et al. |
| 2011/0028780 A1 | 2/2011 | Lanza |
| 2011/0117062 A1 | 5/2011 | Klimanskaya et al. |
| 2011/0117063 A1 | 5/2011 | Klimanskaya et al. |
| 2011/0143441 A1 | 6/2011 | West et al. |
| 2011/0150842 A1 | 6/2011 | Lanza et al. |
| 2011/0171185 A1 | 7/2011 | Klimanskaya et al. |
| 2011/0183415 A1 | 7/2011 | Chung et al. |
| 2011/0256622 A1 | 10/2011 | West et al. |
| 2011/0274662 A1 | 11/2011 | Malcuit et al. |
| 2011/0286978 A1 | 11/2011 | Klimanskaya et al. |
| 2012/0184035 A1 | 7/2012 | Agarwal et al. |
| 2012/0196769 A1 | 8/2012 | West et al. |
| 2013/0022680 A1 | 1/2013 | Klimanskaya et al. |
| 2013/0041348 A1 | 2/2013 | Jacoby et al. |
| 2013/0053278 A1 | 2/2013 | West et al. |
| 2013/0065307 A1 | 3/2013 | Cibelli |
| 2013/0104253 A1 | 4/2013 | Chapman |
| 2013/0149284 A1 | 6/2013 | Malcuit et al. |
| 2013/0183272 A1 | 7/2013 | Kimbrel et al. |
| 2013/0195806 A1 | 8/2013 | Gay et al. |
| 2013/0302286 A1 | 11/2013 | Klimanskaya et al. |
| 2013/0302288 A1 | 11/2013 | Klimanskaya et al. |
| 2013/0302426 A1 | 11/2013 | Klimanskaya et al. |
| 2013/0302824 A1 | 11/2013 | Klimanskaya et al. |
| 2013/0316451 A1 | 11/2013 | Klimanskaya et al. |
| 2013/0316452 A1 | 11/2013 | Klimanskaya et al. |
| 2014/0057348 A1 | 2/2014 | West et al. |
| 2014/0072537 A1 | 3/2014 | Kimbrel et al. |
| 2014/0271590 A1 | 9/2014 | Feng et al. |
| 2014/0294778 A1 | 10/2014 | Lanza et al. |
| 2014/0294779 A1 | 10/2014 | Klimanskaya et al. |
| 2014/0356432 A1 | 12/2014 | Klimanskaya et al. |
| 2014/0356952 A1 | 12/2014 | Chung et al. |
| 2014/0370007 A1 | 12/2014 | McCabe et al. |
| 2014/0377865 A1 | 12/2014 | Lanza et al. |
| 2015/0086512 A1 | 3/2015 | Malcuit et al. |
| 2015/0175960 A1 | 6/2015 | Lanza et al. |
| 2015/0209126 A1 | 7/2015 | Lanza |
| 2015/0232808 A1 | 8/2015 | West et al. |
| 2015/0272994 A1 | 10/2015 | Kimbrel et al. |
| 2015/0313944 A1 | 11/2015 | Feng et al. |
| 2015/0328261 A1 | 11/2015 | Klimanskaya et al. |
| 2015/0366915 A1 | 12/2015 | Gay et al. |
| 2016/0022736 A1 | 1/2016 | Feng et al. |
| 2016/0030490 A1 | 2/2016 | Lanza et al. |
| 2016/0038543 A1 | 2/2016 | Kimbrel et al. |
| 2016/0175361 A1 | 6/2016 | Lanza et al. |
| 2016/0175362 A1 | 6/2016 | Lanza et al. |
| 2017/0152475 A9 | 6/2017 | West et al. |
| 2017/0204368 A1 | 7/2017 | Lanza et al. |
| 2017/0240857 A1 | 8/2017 | Chung et al. |
| 2017/0252374 A1 | 9/2017 | Kimbrel et al. |
| 2017/0274019 A1 | 9/2017 | Wang et al. |
| 2018/0008640 A1 | 1/2018 | Feng et al. |
| 2018/0023052 A1 | 1/2018 | Klimanskaya et al. |
| 2018/0064761 A1 | 3/2018 | Klimanskaya et al. |
| 2018/0072989 A1 | 3/2018 | McCabe et al. |
| 2018/0318353 A1 | 11/2018 | Feng et al. |
| 2019/0030168 A1 | 1/2019 | Gay et al. |
| 2019/0060370 A1 | 2/2019 | Lanza et al. |
| 2019/0062698 A1 | 2/2019 | Chung et al. |
| 2019/0062703 A1 | 2/2019 | Malcuit et al. |
| 2019/0175656 A1 | 6/2019 | Kimbrel et al. |
| 2019/0282622 A1 | 9/2019 | Klimanskaya et al. |
| 2019/0290701 A1 | 9/2019 | Lanza et al. |
| 2019/0321414 A1 | 10/2019 | Lanza et al. |
| 2019/0358330 A9 | 11/2019 | Gay et al. |
| 2020/0023011 A1 | 1/2020 | Feng et al. |
| 2020/0113938 A1 | 4/2020 | Malcuit et al. |
| 2020/0181567 A1 | 6/2020 | West et al. |
| 2020/0405767 A1 | 12/2020 | Gay et al. |
| 2021/0060062 A9 | 3/2021 | Malcuit et al. |
| 2021/0102164 A1 | 4/2021 | Klimanskaya |
| 2021/0161964 A1 | 6/2021 | Feng et al. |
| 2021/0182552 A1 | 6/2021 | Kimbrel et al. |
| 2021/0275673 A1 | 9/2021 | Gay et al. |
| 2021/0308187 A1 | 10/2021 | Klimanskaya et al. |
| 2022/0049217 A1 | 2/2022 | Malcuit et al. |

FOREIGN PATENT DOCUMENTS

| | | |
|---|---|---|
| WO | WO 2001/000650 A1 | 1/2001 |
| WO | WO 2001/018236 A1 | 3/2001 |
| WO | WO 2001/032015 A1 | 5/2001 |
| WO | WO 2001/045500 A1 | 6/2001 |

(56) References Cited

FOREIGN PATENT DOCUMENTS

| | | |
|---|---|---|
| WO | WO 2001/046401 A1 | 6/2001 |
| WO | WO 2002/072762 A2 | 9/2002 |
| WO | WO 2002/073188 A1 | 9/2002 |
| WO | WO 2003/018760 A2 | 3/2003 |
| WO | WO 2004/060056 A2 | 7/2004 |
| WO | WO 2005/068610 A1 | 7/2005 |
| WO | WO 2005/070011 A2 | 8/2005 |
| WO | WO 2006/052646 A2 | 5/2006 |
| WO | WO 2006/080952 A2 | 8/2006 |
| WO | WO 2007/019398 A1 | 2/2007 |
| WO | WO 2007/047894 A2 | 4/2007 |
| WO | WO 2007/130664 A2 | 11/2007 |
| WO | WO 2008/103462 A2 | 8/2008 |
| WO | WO 2009/051671 A1 | 4/2009 |
| WO | WO 2009/085212 A1 | 7/2009 |
| WO | WO 2010/138517 A1 | 12/2010 |
| WO | WO 2011/063005 A2 | 5/2011 |
| WO | WO 2012/012803 A2 | 1/2012 |
| WO | WO 2013/074681 A1 | 5/2013 |
| WO | WO 2013/082543 A1 | 6/2013 |
| WO | WO 2013/086236 A2 | 6/2013 |
| WO | WO 2014/100779 A1 | 6/2014 |
| WO | WO 2014/145108 A1 | 9/2014 |
| WO | WO 2016/037159 A1 | 3/2016 |
| WO | WO 2016/154357 A1 | 9/2016 |
| WO | WO 2017/031312 A1 | 2/2017 |

OTHER PUBLICATIONS

International Preliminary Report on Patentability dated Oct. 5, 2017 for Application No. PCT/US2016/023839.
Bergmann et al., Inhibition of the ATP-driven proton pump in RPE lysosomes by the major lipofuscin fluorophore A2-E may contribute to the pathogenesis of age-related macular degeneration. FASEB Journal, Mar. 2004, vol. 18, pp. 562-564.
Finnemann et al., Phagocytosis of rod outer segments by retinal pigment epithelial cells required alpha(v)beta5 integrin for binding but not for internalization. Proc. Natl. Acad. Sci. USA. Nov. 25, 1997;94(24): 129327-7.
Gordiyenko et al., Silencing of the CHM gene alters phagocytic and secretory pathways in the retinal pigment epithelium. Investigative Ophthalmol Vis Sci. Feb. 2010;51(2):1143-50.
Guo et al., ABCF1 extrinsically regulates retinal pigment epithelial cell phagocytosis. Mol Biol Cell. Jun. 15, 2015;26:2311-20.
Lei et al., Accumulation and autofluorescence of phagocytized rod outer segment material in macrophages and microglial cells. Mol Vision. 2012;18:103-13. Epub Jan. 17, 2012.
Lin et al., Study of temperature effect on single-cell fluid-phase endocytosis using micro cell chips and thermoelectric devices. $14^{th}$ Intl Conf Miniaturized Syst Chem Life Sci. Oct. 3-7, 2010. Groningen, The Netherlands. pp. 962-964. Retrieved from the internet: http://www.rsc.org/binaries/loc/2010/pdfs/papers/330_0130.pdf.
Mao et al., Analysis of photoreceptor outer segment phagocytosis by RPE cells in culture. Methods Mol Biol. 2013;935:285-95. 12 pages.
Miksa et al., A novel method to determine the engulfment of apoptotic cells by macrophages using pHrodo succinimidyl ester. J. Immunol. Method. Mar. 15, 2009;342(1-2):71-7.
Murase et al., TUDCA promotes phagocytosis by retinal pigment epithelium via MerTK activation. Investigative Ophthalmol Vis Sci. Apr. 2015;56(4):2511-8.
Extended European Search Report for Application No. 21167900.6, dated Jul. 1, 2021.
Ledingham, The Influence of Temperature on Phagocytosis. Proc R Soc Lond B Biol Sci. May 14, 1908; 80(539): 188-195. http://www.jstor.org/stable/80300.
Zhang et al., Study on the dynamic phagocytosis function of retinal pigment epithelial cells and their expression of alpha v beta 5 receptors. Recent Advances in Ophthalmology. May 31, 2007;27(5):327-332. Available at http://med.wanfangdata.com.cn/Paper/Detail/PeriodicalPaper_ykxjz200705002. Last accessed on Apr. 12, 2021.
Zhang et al., Effect of phagocytic load on apoptosis of cultured aged bovine retinal pigment epithelium. International Journal of Ophthalmology. Oct. 31, 2014;14(11):1935-38.
Ohkuma, Endocytosis, pH and H+-pump. Seibutsu Butsuri. 1984;24(3):119-27.

ASSAYS FOR POTENCY OF HUMAN RETINAL PIGMENT EPITHELIUM (RPE) CELLS AND PHOTORECEPTOR PROGENITORS

RELATED APPLICATIONS

This application is a national stage filing under 35 U.S.C. § 371 of International Application No. PCT/US2016/023839, filed Mar. 23, 2016, which was published under PCT Article 21(2) in English, and which claims the benefit under 35 U.S.C. § 119(e) of U.S. Provisional Application Ser. No. 62/136,660, filed Mar. 23, 2015, entitled "IMPROVED ASSAYS FOR POTENCY OF HUMAN RPE CELLS AND PHOTORECEPTOR PROGENITORS", the entire contents of each of which are incorporated herein by reference.

FIELD OF INVENTION

This invention relates to the use of an in vitro cell-based method to measure phagocytosis of photoreceptor outer rod segments.

BACKGROUND

The retinal pigment epithelium (RPE) is the pigmented cell layer outside the neurosensory retina between the underlying choroid (the layer of blood vessels behind the retina) and overlying retinal visual cells (e.g., photoreceptors—rods and cones). The RPE is critical to the function and health of photoreceptors and the retina. The RPE maintains photoreceptor function by recycling photopigments, delivering, metabolizing, and storing vitamin A, phagocytosing rod photoreceptor outer segments, transporting iron and small molecules between the retina and choroid, maintaining Bruch's membrane and absorbing stray light to allow better image resolution. See. e.g., WO 2009/051671; Engelmann and Valtink (2004) "RPE Cell Cultivation." *Graefe's Archive for Clinical and Experimental Ophthalmology* 242 (1): 65-67; Irina Klimanskaya, *Retinal Pigment Epithelium Derived From Embryonic Stem Cells*, in STEM CELL ANTHOLOGY 335-346 (Bruce Carlson ed., 2009).

Degeneration of the RPE can cause retinal detachment, retinal dysplasia, or retinal atrophy that is associated with a number of vision-altering ailments that result in photoreceptor damage and blindness such as choroideremia, diabetic retinopathy, macular degeneration (including age-related macular degeneration, AMD) and Stargardt's macular dystrophy (SMD), the latter two being two of the leading causes of adult and juvenile blindness in the world, respectively. Although both are currently untreatable, there is evidence in preclinical models of macular degeneration that transplantation of hESC-derived RPE can rescue photoreceptors and prevent visual loss (Lund R D, Wang S, Klimanskaya I, et al. Human embryonic stem cell-derived cells rescue visual function in dystrophic rats. Cloning and Stem Cells 2006; 8,189-199; Lu B, Malcuit C, Wang S, et al. Long-term safety and function of RPE from human embryonic stem cells in preclinical models of macular degeneration. Stem Cells 2009; 21, 2125-2135).

Also contributing to some of the afore-mentioned diseases is the additional loss of post-mitotic neuronal cells. Among these retinal diseases are rod or cone dystrophies, retinal degeneration, retinitis pigmentosa (RP), diabetic retinopathy, macular degeneration, Leber congenital amaurosis and Stargardt disease. In most cases of retinal degeneration, cell loss is primarily in the outer nuclear layer (ONL) which includes rod and cone photoreceptors.

A potential replacement source of photoreceptor cells includes stem cells. Early studies evaluated mouse cells, mouse stem cells or heterogeneous populations of retinal progenitor cells as a possible source of replacement cells for lost photoreceptors. These early studies described transplantation of photoreceptor precursor cells from postnatal day 1 mouse retina (Maclaren et al. Nature 444(9):203-207, 2006), in vitro generation of retinal precursor cells from mouse embryonic stem cells (Ikeda et al. Proc. Natl. Acad. Sci. 102(32):11331-11336, 2005), generation of retinal progenitor cells from postnatal day 1 mouse retinas (Klassen et al. Invest. Ophthal. Vis. Sci. 45(11):4167-4175, 2004), implantation of bone marrow mesenchymal stem cells in an RCS rat model of retinal degeneration (Inoue et al. Exp. Eye Res. 8(2):234-241, 2007), production of retinal progenitor cells, including ganglion cells, amacrine cells, photoreceptors wherein 0.01% of the total cells expressed S-opsin or rhodopsin, bipolar cells and horizontal cells, from the H1 human embryonic stem cell line (Lamba et al. Proc. Natl. Acad. Sci. 10(34):12769-12774, 2006), and induction of induced pluripotent stem cells (iPS) from human fibroblasts to produce retinal progenitor cells (Lamba et al. PLoS ONE 5(1):e8763. doi:10.1371/journal.pone.0008763). None of these approaches produced a homogeneous population of photoreceptor progenitor cells or photoreceptor cells for implantation. None of these approaches produced a homogeneous population of photoreceptor progenitor cells or photoreceptor cells that showed in vivo rod or cone function (e.g., detectable by conferring improvements in visual acuity). Supplies of donor-derived tissue from which photoreceptors and photoreceptor progenitors may be isolated (such as cadavers, fetal tissue, and live animals) are limited. Stem cells can be propagated and expanded in vitro indefinitely, providing a potentially inexhaustible source of non-donor derived cells for human therapy. Differentiation of stem cells into a homogeneous population of photoreceptor progenitors or photoreceptors may provide an abundant supply of non-donor derived cells for implantation and treatment of retinal diseases. The photoreceptor progenitor cells may have phagocytic activity.

Certain subject matter including methods of making RPE cells, compositions of RPE cells, and release assays (including phagocytosis assays) for RPE cells are disclosed in co-owned U.S. application Ser. No. 13/510,426, filed Nov. 17, 2010 and PCT US2012/65091, such teachings incorporated by reference herein. Certain subject matter including methods of making photoreceptor progenitors, and compositions of photoreceptor progenitors and methods of testing function (including phagocytosis assays) are disclosed in co-owned PCT US2014/029790, such teachings incorporated by reference herein.

SUMMARY

FITC-labeled Photoreceptor Outer Segments (OS) (usually bovine or porcine) have been used to study phagocytosis by retina pigment epithelium (RPE) in vitro. However, most of the quantitative methods used for phagocytosis assessment (FACS, fluorescence plate reader) do not differentiate between surface-bound and internalized particles and thus do not allow one to specifically address mechanisms involved in surface receptor binding and internalization stages of phagocytosis. Additionally, FITC fluorescence is pH-sensitive and is significantly reduced at pH below 6 while the pH of lysosomes and phagosomes fused with lysosomes is below 5. Thus fluorescence of FITC-labeled OS may not be truly representative of the amount of internalized OS.

Provided herein is a more sensitive and accurate assay for detecting internalized phagocytosis of photoreceptor outer segments, an important measure of RPE cell and photoreceptor progenitor function and consequently an important release criteria for RPE cells and photoreceptor progenitors to be used in treating retinal diseases, such as rod or cone dystrophies, retinal degeneration, retinitis pigmentosa, choroideremia, diabetic retinopathy, macular degeneration (including age-related macular degeneration and myopic macular degeneration), Leber congenital amaurosis and Stargardt disease (fundus flavimaculatus). See, e.g., WO 2009/051671.

The RPE cells described herein are functional after transplantation. To this end, the RPE cells form a monolayer between the neurosensory retina and the choroid in the subject (or patient) receiving the transplanted cells. The RPE cells may also supply nutrients to adjacent photoreceptors and dispose of shed photoreceptor outer segments by phagocytosis.

RPE cells suitable for transplantation may be selected based on a number of functional and/or phenotypic characteristics, including but not limited to phagocytosis activity. For example, RPE cells suitable for transplantation may be assessed according to their phagocytosis activity as well as their proliferative potential. For example, the RPE cells may have greater proliferative potential than cells derived from eye donors (e.g., the RPE cells are "younger" than those of eye donors). This allows the RPE cell described herein to have a longer useful lifespan than cells derived from eye donors.

One of the key parameters to RPE cell potency in the clinical context is the quantitative measure of the outer segment phagocytosis activity of the pharmaceutical preparations of RPE cells. The phagocytosis of the outer segments results in the accumulation of the phagocytosed cell fragments in low-pH compartments in the RPE cells. The present invention provides for photoreceptor outer segments that have been associated (i.e., covalently or non-covalently) with a detectable marker which is detectable spectrophotometrically to provide a spectrophotometric signal, the detectable marker being selective to have a first spectrophotometric signal when present at a neutral pH or physiological pit i.e., a pH of 7 to 7.5, and second spectrophotometric signal when present in the low pH environment of an intracellular compartment, such as a lysosome, phagosome, endosome, or the like. The difference between the first and second spectrophotometric signals may be one or more of the degree of fluorescence emission (increased intensity at low pH relative to neutral pH), a change in the fluorescence emission wavelength between neutral and low pH, a change in the fluorescence excitation wavelength between neutral and low pH, or the like.

In certain embodiments, the detectable marker can be a fluorescent pH sensor, such as fluorescent dye. Exemplary fluorescent dyes that can be used in the instant invention may be a fluorescent dye moiety having an amino group (aliphatic or aromatic) as the pH sensitive indicator moiety, i.e., an amine which is unprotonated at the pH of the culture media in which the RPE cells and outer segments are incubated together (i.e., a neutral pH or physiological pH), and becomes protonated at the pH of the intracellular compartment into which the outer segments are absorbed by the cells such as the RPE cells by phagocytosis. When such a dye adsorbs a photon, creating an excited electronic state, the electron of the amino group's unshared pair transfers to the orbital vacated by excitation. Such an electron transfer, referred to as Photoinduced Electron Transfer (PET) prevents the excited molecule from emission transition, thus the fluorescence of the dye is quenched. Protonation of the amino group changes the nature and energy of the pair's orbital and stops the PET. As a result, the fluorescent reporter moiety responds to a pH change. Because protonation of the amino group cancels the quenching, the PET-based sensors become more fluorescent as pH decreases.

In certain embodiments, the fluorescent dye is a rhodamine-based pH sensitive dye, such as described in WO 2005/098437. These dyes have a benzene ring substituted ortho to the xanthene moiety by —OH or —SH (or their depronated forms). These dyes display a pH-dependency similar to amine PET indicators but were designed to have pKa values of less than 6 based on a perceived need for a pH sensor that would target cell compartments with a pH of less than 6.

In another exemplary embodiment, the fluorescent marker is a pH-sensitive fluorescent nanoparticle. pH-sensitive fluorescent nanoparticles primarily employ polymers conjugated with small molecular pH-sensitive dyes (Srikun, D., J. Chem. Sci. 2011, 2, 1156; Benjaminsen, R. V., ACS Nano 2011, 5, 5864; Albertazzi, L., J. Am. Chem. Soc. 2010, 132, 18158; Urano, Y., Nat. Med. 2009, 15, 104) or the use of pH-sensitive linkers to conjugate pH-insensitive dyes (Li, C, Adv. Fund. Mater. 2010, 20, 2222; Almutairi, J. Am. Chem. Soc. 2007, 130, 444). To further illustrate, WO 2013152059 describes pH-tunable, highly activatable multicolored fluorescent nanoplatforms which can be adapted for use in the present assays.

Thus, provided herein in one aspect is a method for assessing phagocytosis activity comprising incubating cells with photoreceptor outer segments (POS) for a time and temperature sufficient for the cells to phagocytose the POS, wherein the POS fluoresce more at an acidic pH than at a higher pH, and detecting fluorescence intensity of the cells after incubation, wherein an increase in fluorescence compared to a control indicates phagocytosis of the POS by the cells.

In some embodiments, the cells are incubated with the POS at a temperature ranging from about room temperature to about 37° C. or about room temperature to about 40° C. In some embodiments, the cells are incubated with the POS at about room temperature, at about physiological temperature, or at about 37° C.

In some embodiments, the control is cells incubated with the POS at below room temperature. In some embodiments, the control is cells incubated with the POS at 4° C.

Also provided herein is a method for assessing phagocytosis activity of an adherent cell population comprising incubating an adherent cell population with photoreceptor outer segments (POS) for a time and temperature sufficient for cells in the cell population to phagocytose the POS, wherein the POS fluoresce more at an acidic pH than at a higher pH, and detecting fluorescence intensity of the cell population after incubation, wherein an increase in fluorescence compared to a control indicates phagocytosis of the POS by the cells.

In some embodiments, the adherent cell population is incubated with the POS at a temperature ranging from about 17-40° C., or from about 25-40° C., or from about 34-40° C., or at a temperature of about 37° C. In some embodiments, the control is a cell population incubated with the POS at a temperature of about 10-16° C. In some embodiments, the control is a cell population incubated with the POS at a temperature of about 12-15° C.

Also provided herein is a method for assessing phagocytosis activity comprising providing photoreceptor outer segments (POS) labeled with a fluorescent label having an altered fluorescence signal when internalized by phagocytosis into a low compartment in a cell relative to the fluorescence signal when present extracellularly; incubating test cells with the labeled POS under conditions permissive for the phagocytosis of the labeled POS; and detecting the altered fluorescence, if any, in the test cells after incubation with the labeled POS, and quantifying the phagocytosis activity of the test cells therefrom.

In some embodiments, the altered fluorescence signal (when the label is internalized by phagocytosis into a low pH compartment) is an increase in intensity of the fluorescence signal relative to the when the fluorescent label is present extracellularly. In some embodiments, the altered fluorescence signal (when the label is internalized by phagocytosis into a low pH compartment) is detectable by flow cytometry. In some embodiments, the altered fluorescence signal distinguishes between labeled POS internalized by phagocytosis and labeled POS bound on the surface of the test cells but not internalized. In some embodiments, the altered fluorescence signal detected in the test cells is compared to a control cell population incubated with labeled POS in order to quantify the phagocytosis activity of the test cells.

In some embodiments, the test cells are incubated with labeled POS at about room temperature, at about physiological temperature, at about 37° C., at about 15-40° C., or between room temperature and 37° C., or between room temperature and 40° C.

In some embodiments, the control cell population is incubated with labeled POS at a below room temperature, including at about 4° C.

Also provided is a method for assessing phagocytosis activity comprising providing photoreceptor outer segments (POS) labeled with a fluorescent label having an altered fluorescence signal when internalized by phagocytosis into a low pH compartment in a cell relative to the fluorescence signal when present extracellularly; incubating adherent test cells with the labeled POS under conditions permissive for the phagocytosis of the labeled POS; and detecting the altered fluorescence, if any, in the adherent test cells after incubation with the labeled POS, and quantifying the phagocytosis activity of the adherent test cells therefrom.

In some embodiments, the test cells are incubated with the POS at a temperature ranging from about 17-40° C., or from about 25-40° C., or from about 34-40° C., or at a temperature of about 37° C. In some embodiments, the altered fluorescence signal detected in the adherent test cells is compared to a control cell population incubated with labeled POS at a temperature that maintains the viability of the cells yet induces low or no phagocytosis, optionally such a temperature may range from about 12-15° C., in order to quantify the phagocytosis activity of the test cells. In some embodiments, the control cell population is incubated with the POS at a temperature of about 10-16° C.

Also provided herein is a labeled photoreceptor outer segment (POS) preparation for assessing phagocytic activity of a test cell population, the POS being labeled with a fluorescent label having an altered fluorescence signal when internalized by phagocytosis into a low pH compartment in a cell relative to the fluorescence signal when the fluorescent label is present extracellularly. In some embodiments, the altered fluorescence signal (when the label is internalized by phagocytosis into a low pH compartment) is an increase in intensity of the fluorescence signal relative to the when present extracellularly. In some embodiments, the altered fluorescence signal (when the label is internalized by phagocytosis into a low pH compartment) is detectable by flow cytometry. In some embodiments, the fluorescent label is pHrodo® Red. In some embodiments, the POS are labeled with pHrodo® Red and pHrodo® Red E. coli BioParticles.

Also provided herein is a method for measuring phagocytosis activity in a cell population comprising measuring test fluorescence in a test cell population contacted with non-FITC fluorescently labeled photoreceptor outer segments (POS), and comparing the measured test fluorescence to a control fluorescence, wherein the non-FITC fluorescently labeled POS fluoresces at an acidic pH but does not fluoresce or minimally fluoresces at higher pH.

In some embodiments, the test cell population is contacted with non-FITC fluorescently labeled POS at a temperature ranging from about room temperature to about physiological temperature, including for example about 37° C. (i.e., about room temperature to about 37° C.), or about room temperature to about 40° C. In some embodiments, the test cell population is contacted with non-FITC fluorescently labeled POS at a temperature between about 15-40° C., or at about physiological temperature, including for example about 37° C. In some embodiments, the control fluorescence is fluorescence of a cell population contacted with the non-FITC fluorescently labeled POS at below room temperature. In some embodiments, the control fluorescence is fluorescence of a cell population contacted with the non-FITC fluorescently labeled POS at 4° C.

Also provided herein is a method for measuring phagocytosis activity in an adherent cell population comprising measuring test fluorescence in an adherent test cell population contacted with non-FITC fluorescently labeled photoreceptor outer segments (POS), and comparing the measured test fluorescence to a control fluorescence, wherein the non-FITC fluorescently labeled POS fluoresces at an acidic pH but does not fluoresce or minimally fluoresces at higher pH.

In some embodiments, the test cell population is contacted with non-FITC fluorescently labeled POS at a temperature ranging from about 17-40° C., or from about 25-40° C., or from about 34-40° C., or a temperature of about 37° C.

In some embodiments, the control fluorescence is fluorescence of an adherent cell population contacted with the non-FITC fluorescently labeled POS at temperature of about 12-15° C. In some embodiments, the control fluorescence is fluorescence of an adherent cell population contacted with the non-FITC fluorescently labeled POS at temperature of about 10-16° C.

Also provided herein is a method for measuring phagocytosis activity comprising (1) measuring a test fluorescence in a first aliquot of a cell population incubated with fluorescently labeled photoreceptor outer segments (POS) that are labeled with pHrodo® Red dye at a temperature ranging from about room temperature to about physiological temperature including for example 37° C., or about room temperature to about 40° C., and (2) measuring a control fluorescence in a second aliquot of the cell population incubated with fluorescently labeled POS that are labeled with pHrodo® Red dye at below room temperature, wherein a test fluorescence that is greater than a control fluorescence indicates phagocytosis activity of the cell population.

Also provided herein is a method for measuring phagocytosis activity comprising (1) measuring a test fluorescence in a first aliquot of an adherent cell population incubated with fluorescently labeled photoreceptor outer segments (POS) that are labeled with pHrodo® Red dye, and (2) measuring a control fluorescence in a second aliquot of the adherent cell population incubated with fluorescently labeled POS that are labeled with pHrodo® Red dye, wherein a test fluorescence that is greater than a control fluorescence indicates phagocytosis activity of the cell population.

In some embodiments, the first aliquot of the adherent cell population is incubated with the labeled POS at a temperature ranging from about 17-40° C., or from about 25-40° C., or from about 34-40° C., or a temperature of about 37° C. In some embodiments, second aliquot of the adherent cell population is incubated with the labeled POS at a temperature ranging from about 10-16° C. or 12-15° C.

Also provided herein is a method for measuring phagocytosis activity comprising (1) measuring a test fluorescence in a first aliquot of a cell population incubated with pHrodo® Red labeled photoreceptor outer segments (POS) alone or with pHrodo® Red E. coli BioParticles, at a temperature ranging from about room temperature to about physiological temperature including 37° C., or about room temperature to about 40° C., and (2) measuring a control fluorescence in a second aliquot of the cell population incubated with pHrodo® Red labeled photoreceptor outer segments (POS) alone or with pHrodo® Red E. coli BioParticles, at below room temperature, including 4° C., wherein a test fluorescence that is greater than a control fluorescence indicates phagocytosis activity of the cell population.

Also provided herein is a method for measuring phagocytosis activity comprising (1) measuring a test fluorescence in a first aliquot of an adherent cell population incubated with pHrodo® Red labeled photoreceptor outer segments (POS) alone or with pHrodo® Red E. coli BioParticles, at a temperature ranging from about 17-40° C., or from about 25-40° C., or from about 34-40° C., or a temperature of about 37° C., and (2) measuring a control fluorescence in a second aliquot of the adherent cell population incubated with pHrodo© Red labeled photoreceptor outer segments (POS) alone or with pHrodo® Red E. coli BioParticles, at temperature ranging from about 10-16° C. or about 12-15° C., wherein a test fluorescence that is greater than a control fluorescence indicates phagocytosis activity of the cell population.

Various embodiments apply equally to the any and all of the afore-mentioned aspects. These are recited below.

In some embodiments, the cells, cell population, test cells, or test cell population are incubated with the POS at about room temperature, at about physiological temperature, or at about 37° C., or about room temperature to about 40° C., or about room temperature to about 37° C., or about 15-40° C. In some embodiments, the cells, cell population, test cells, or test cell population are incubated with labeled POS at a temperature ranging from about 17-40° C., or from about 25-40° C., or from about 34-40° C., or at a temperature of about 37° C.

In some embodiments, the control cells, control cell population, control test cells, or control test cell population are incubated with the POS at a temperature that is less than room temperature, a temperature ranging from about 10-16° C. or from about 12-15° C., or a temperature of about 4° C.

In some embodiments, the cells, cell population, test cells, or test cell population comprise retinal pigmented epithelial (RPE) cells. In some embodiments, the cells, cell population, test cells, or test cell population comprise photoreceptor progenitor cells. In some embodiments, the cells, cell population, test cells, or test cell population are human cells.

In some embodiments, the cells, cell population, test cells, or test cell population are produced by in vitro differentiation of pluripotent stem cells.

In some embodiments, the cells, cell population, test cells, or test cell population were cryopreserved and thawed prior to use.

In some embodiments, the cells, cell population, test cells, or test cell population is provided as a confluent monolayer.

In some embodiments, the cells, cell population, test cells, or test cell population are or is enzyme digested prior to use.

In some embodiments, the cells, cell population, test cells, or test cell population is or are provided as an adherent cell population.

In some embodiments, the POS are fragmented POS. In some embodiments, the POS are sonicated POS.

In some embodiments, the fluorescent label is pHrodo® Red. Thus, in some embodiments, the POS are labeled with pHrodo® Red dye. In some embodiments, the POS are labeled with pHrodo® Red and pHrodo® Red E. coli BioParticles. In some embodiments, the cells are incubated with pHrodo® Red labeled POS and pHrodo® Red E. coli BioParticles.

In some embodiments, fluorescence is detected by flow cytometry. In some embodiments, fluorescence is detected using a plate reader.

In some embodiments, the cells are incubated with the POS for about 15-30 hours, or 16-20 hours, or 20-28 hours.

In some embodiments, the cells are provided as a cell culture. In some embodiments, the cells are a confluent cell culture.

It is to be understood that the test and control cells may be different aliquots of the same cell population.

In another aspect, this disclosure provides an isolated cell population characterized as having a rate of phagocytosis of photoreceptor outer segments (POS) that is at least 50% greater than a rate of phagocytosis of POS for an equivalent number of primary cells. In some embodiments, the cell population is an RPE cell population. In some embodiments, the cell population is an RPE cell population obtained by in vitro differentiation of pluripotent stem cells and the primary cells are RPE cells from isolated adult eyes. In some embodiments, the cell population is photoreceptor progenitors.

These and various other aspects and embodiments will be described in greater detail herein.

DETAILED DESCRIPTION

Figure 1A:
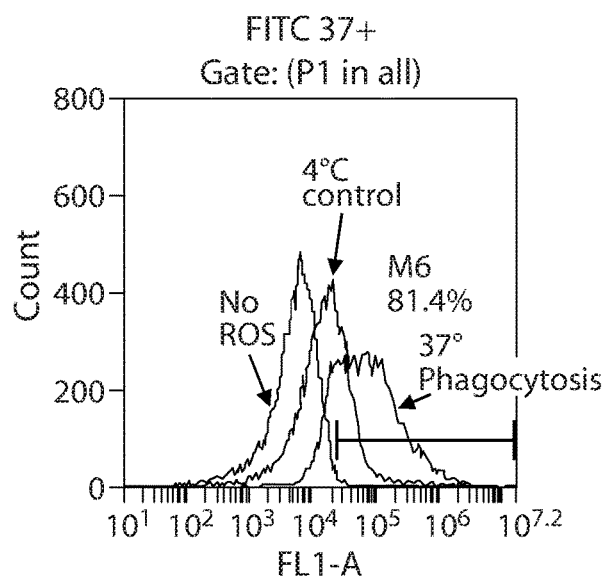
FIGS. 1A-C. FACS analysis of phagocytosis by RPE. (A) FITC-labeled ROS. (B) pHrodo®-labeled ROS. Shown are the plots for the control in which no ROS were added, the control in which ROS were added and the cells incubated at 4° C., and the test in which ROS were added and the cells incubated at 37° C. (C) pHrodo®-labeled BioParticles (bacterial fragments). Shown are the plots for the control in which no particles were added, the control in which particles were added and the cells incubated at 4° C., and the test in which particles were added and the cells incubated at 37° C. It is to be understood that POS and ROS are used interchangeably herein to refer to the photoreceptor rod outer segments.

Phagocytosis (potency assay) may be assessed by quantitative fluorescence activated cell sorting (FACS) analysis of RPE cultures exposed to photoreceptor outer segments (POS) labeled with pHrodo® Red dye (Life Technologies, Molecular Probes).

Phagocytosis may be assessed by a FACS-based assay using POS labeled with pHrodo® Red dye (Life Technologies, Molecular Probes). The dye and the POS so labeled fluoresce when internalized in the reduced pH environment of intracellular phagosomes. The POS may be labeled as described herein.

In some embodiments, the RPE cell cultures are confluent. As an example, confluent RPE may be cultured in multiwell plates, and may be incubated with POS labeled with pHrodo® Red dye, optionally in the presence of $CO_2$-independent medium (invitrogen). The incubation may occurs for any time sufficient for the RPE cells to phagocytose the POS. As an example, the incubation may occur for 16-20 hours. The assay occurs at a temperature sufficient for the RPE cells to phagocytose the POS. In some embodiments, the assay occurs at about physiological temperature or about 37° C. In some embodiments, the assay occurs at room temperature. In some embodiments, the control (or negative control) plates are incubated at 4° C. Cells may be examined under the microscope, fluorescence measured using plate readers, and/or the cells may be harvested after enzyme digestion (e.g., trypsin digestion) and analyzed by flow cytometry.

An exemplary, non-limiting, assay is as follows:
RPE manufactured from pluripotent stem cells (such as but not limited to ES cell and iPS cells) as described previously are tested for their ability to phagocytose. The cryopreserved RPE may be previously frozen and thawed prior to use. The RPE cells are seeded in culture in a suitable medium and grown to confluence and maintained in culture prior to testing for their ability to phagocytose POS labeled with pHrodo® Red dye which fluoresces when internalized in the acidic environment of phagosomes of the RPE cells. RPE cells are incubated with the labeled POS at 37° C. to permit phagocytosis, or at 4° C. as a negative control. Shifts in fluorescence intensity may be detected by flow cytometry for the cells incubated at 37° C., indicating phagocytosis of the labeled POS. Statistical integration of the peaks yield the percentages of phagocytic positive cells for each lot of RPE cells and incubation temperature.

As will be understood by this disclosure, phagocytosis is detected by incubating RPE cells with labeled POS that fluoresce in the red spectrum in the acidic phagosome environment. Percentages of phagocytic positive cells may be shown for cells incubated with at 37° C. or at 4° C. (negative control), as detected by flow cytometry.

The resulting RPE cell population may be characterized based on its phagocytic activity according to the methods provided herein. Rates of phagocytosis may be determined and the RPE cells so characterized. For example, the RPE cells may be characterized as having a rate of phagocytosis of photoreceptor outer segments (POS) that is at least 50 percent greater than the rate of phagocytosis of POS for an equivalent number of RPE cells isolated adult eyes, or at least 75, 100, 150 or 200 percent greater than the rate of phagocytosis of POS for an equivalent number of RPE cells isolated adult eyes. Alternatively or additionally, the RPE cells may be characterized by a rate of phagocytosis of photoreceptor outer segments (POS) that is at least 20 percent of the total concentration of POS after 24 hours, or at least 25, 30, 25, 40 or 50 percent of the total concentration of POS after 24 hours.

Thus, using the methods described herein, RPE cell populations have been achieved that have a rate of phagocytosis of photoreceptor outer segments (POS) that is at least 50 percent greater than the rate of phagocytosis of POS for an equivalent number of RPE cells isolated adult eyes (i.e., human adult patients from the age of 25-80, more preferably adults from the age of 50-80), and more preferably at least 75, 100, 150 or even 200 percent greater.

Using the methods described herein, RPE cell populations have been achieved that have a rate of phagocytosis of photoreceptor outer segments (POS) that is at least 20 percent of the total concentration of POS after 24 hours, and more preferably at least 25, 30, 25, 40 or even 50 percent of the total concentration of POS after 24 hours.

Thus, this disclosure provides in one aspect a method comprising detecting or measuring fluorescence in an RPE cell (or an RPE cell population) contacted with fluorescently labeled photoreceptor outer segments (POS) that are non-FITC fluorescently labeled (regarded as the test fluorescence, or generally "test")) and comparing the detected or measured fluorescence to a control (regarded as the control fluorescence or generally "control"). The test may be performed at a temperature that is about room temperature, or a temperature between about 15-40° C., or at about a physiological temperature (e.g., at about 37° C.). The control may be performed at about 4° C. Thus, the control fluorescence may be the fluorescence that is detected or measured following incubation of RPE cells with non-FITC labeled POS at 4° C. Non-FITC fluorescently labeled POS are POS that are labeled with a fluorophore that is not FITC. The non-FITC fluorescent label is a label that fluoresces at an acidic pH such as the pH of the phagosomes, and particularly phagosomes of RPE cells but that does not fluoresce or that fluoresces minimally at higher pHs such as neutral pH (or an extracellular environment pH). The non-FITC fluorescent label are useful in discriminating between surface labeling and internalized labels. An example of such a fluorophore is pHrodo® Red dye (Life Technologies, Molecular. Probes). A higher degree of phagocytosis in the test is indicated by a higher fluorescence as compared to the control.

Thus, in another aspect, the disclosure provides a method comprising (1) detecting or measuring fluorescence in a first aliquot of an RPE cell (or an RPE cell population) contacted with (and incubated with) fluorescently labeled photoreceptor outer segments (POS) that are labeled with pHrodo® Red dye at 37° C. (regarded as the test fluorescence, or generally "test")), and (2) detecting or measuring fluorescence in second aliquot of an RPE cell (or an RPE cell population) contacted with (and incubated with) fluorescently labeled photoreceptor outer segments (POS) that are labeled with pHrodo® Red dye at 4° C. (regarded as the control fluorescence, or generally "control")), and (3) optionally comparing, determining and/or quantifying the test and control fluorescences wherein a test fluorescence that is greater than a control fluorescence is an indication of phagocytosis activity of the RPE cell (or cell population).

It is to be understood that the methods described herein may also be used to assay phagocytosis activity in photoreceptor progenitor (or precursor) cells.

In certain embodiments, the RPE and photoreceptor progenitor cells have phagocytic activity, such as the ability to phagocytose isolated pHrodo® Red photoreceptor outer segments, pHrodo® Red $E.$ $coli$ BioParticles or both, and the methods provided herein assay one or more of these functions.

In an aspect, the present disclosure provides an assay for determining the potency of a pharmaceutical composition comprising: a plurality of retinal pigment epithelial (RPE) cells or photoreceptor progenitor cells; and a pharmaceutically acceptable carrier. In one embodiment, the average melanin content of said plurality of RPE cells is less than 8 pg/cell. Said RPE cells or photoreceptor progenitor cells may be contained in a suspension, gel, colloid, matrix, substrate, scaffold, or graft.

Said pharmaceutically acceptable carrier may comprise a sterile solution having an osmolality of between about 290 mOsm/kg and about 320 mOsm/kg, or between about 300 mOsm/kg and 310 mOsm/kg or about 305 mOsm/kg. Said pharmaceutically acceptable carrier may comprise a balanced salt solution. Said balanced salt solution may comprise, consists of, or consist essentially of, in each mL, sodium chloride 7.14 mg, potassium chloride 0.38 mg, calcium chloride dihydrate 0.154 mg, magnesium chloride hexahydrate 0.2 mg, dibasic sodium phosphate 0.42 mg, sodium bicarbonate 2.1 mg, dextrose 0.92 mg, glutathione disulfide (oxidized glutathione) 0.184 mg, and hydrochloric acid and/or sodium hydroxide (to adjust pH to approximately 7.4) in water.

The volume of said pharmaceutical composition may be between about 100 µL and 1000 µL or may be at least about 150 µL. Said pharmaceutical composition may comprise between about 1,000 and about $1 \times 10^9$ viable RPE cells. Said pharmaceutical composition may comprise between about 333 viable RPE cells/µL and about 2,000 viable RPE cells/µL, between about 444 viable RPE cells/µL and about 1766 viable RPE cells/µL, about 333 viable RPE cells/µL, about 444 viable RPE cells/µL, about 666 viable RPE cells/µL, about 888 viable RPE cells/µL, about 999 viable RPE cells/µL, or about 1,333 viable RPE cells/µL.

The concentration of RPE cells in said pharmaceutical composition may be sufficiently high that no more than about 30% of said RPE cells lose viability in 60 minutes, and optionally no more than about 10% of said RPE cells lose viability in 4 hours. Said concentration of RPE cells may be at least about 1,000 cells/µL, at least about 2,000 cells/µL, between about 1,000-10,000 cells/µL, or between about 2,000-5,000 cells/µL.

The pharmaceutical preparation may comprise less than about 25%, 20%, 15%, 10%, 5%, 1%, 0.5%, 0.1%, 0.01%, 0.001%, or 0.0001% cells that may be not RPE cells.

The average melanin content of said RPE cells may be less than 8 pg/cell, less than 7 pg/cell, less than 6 pg/cell, less than 5 pg/cell, less than 4 pg/cell, less than 3 pg/cell, less than 2 pg/cell and at least 0.1 pg/cell and optionally at least 0.5 pg/cell or 1 pg/cell; between 0.1-8 pg/cell, between 0.1-7 pg/cell, between 0.1-6 pg/cell, between 0.1-5 pg/cell, between 0.1-4 pg/cell, between 0.1-3 pg/cell, between 0.1-2 pg/cell, between 0.1-1 pg/cell, between 1-7 pg/cell, between 0.5-6 pg-cell, or between 1-5 pg/cell.

At least 50%, at least 60%, at least 70%, or at least 80% of the cells in said pharmaceutical composition may be bestrophin+. At least 80%, at least 85%, at least 90%, at least 95%, or at least 99% of the cells in said pharmaceutical composition may be PAX6+ and/or MITF+. At least 80%, at least 85%, at least 90%, at least 95%, or at least 99% of the cells in said pharmaceutical composition may be PAX6+ and/or bestrophin+. At least 80%, at least 85%, at least 90%, at least 95%, or at least 99% of the cells in said pharmaceutical composition may be ZO-1+. At least 50%, at least 60%, or at least 70% of the cells in the pharmaceutical composition may be PAX6+ and bestrophin+. At least 90%, at least 95%, or at least 99% of the cells in said pharmaceutical composition may be PAX6+.

In an exemplary embodiment, no more than about one cell per million cells and optionally no more than two cells per nine million cells in said pharmaceutical composition may be positive for both OCT-4 and alkaline phosphatase (AP) expression.

A needle or an injection cannula may contain at least a portion of said RPE cells. The concentration of said RPE cells upon loading into said needle or injection cannula may be between about 444 viable cells/µL and about 1,766 viable cells/µL. The concentration of viable RPE cells to be delivered from said needle or injection cannula may be between about 333 viable cells/µL and about 1,333 viable cells/µL. The diameter of said needle or injection cannula may be between about 0.3 mm and about 0.9. The diameter of said needle or injection cannula may be between about 0.5 and about 0.6 mm. Said needle or injection cannula may comprise a tip having a diameter between about 0.09 mm and about 0.15 mm. Said cannula may be a MEDONE POLYTIP® Cannula 25/38 g (a 0.50 mm (25 g)×28 mm cannula with 0.12 mm (38 g)×5 mm tip) or a Synergetics Angled 39 g Injection Cannula.

Said RPE cells may comprise RPE cells which have been cryopreserved and thawed.

Said RPE cells may be human.

Said RPE cells, such as human RPE cells, may be produced from any source including pluripotent cells such as embryonic stem cells or induced pluripotent stein cell as well as donor adult or fetal tissue Said pluripotent stem cell may be positive for expression of one or more markers may comprise OCT-4, alkaline phosphatase, Sox2, TDGF-1, SSEA-3, SSEA-4, TRA-1-60, and/or TRA-1-81. Said pluripotent cells may be human pluripotent cells that may be cultured in a multilayer population or embryoid body for a time sufficient for pigmented epithelial cells to appear in said culture. Said time sufficient for pigmented epithelial cells to appear in said culture may comprise at least about 1 week, at least about 2 weeks, at least about 3 weeks, at least about 4 weeks, at least about 5 weeks, at least about 6 weeks, or at least about 7 weeks, at least about 8 weeks. Said multilayer population or embryoid body may be cultured in a medium may comprise DMEM. Said medium may comprise, consists essentially of, or consists of EB-DM. Said pigmented epithelial cells may be isolated and cultured, thereby producing a population of RPE cells. Said isolating may comprise dissociating cells or clumps of cells from the culture enzymatically, chemically, or physically and selecting pigmented epithelial cells or clumps of cells may comprise pigmented epithelial cells. Said embryoid body may be cultured in suspension and/or as an adherent culture (e.g., in suspension followed by adherent culture). Said embryoid body cultured as an adherent culture may produce one or more outgrowths comprising pigmented epithelial cells. Said pluripotent stem cells have reduced HLA antigen complexity. Prior to RPE formation said pluripotent cells may be cultured on a matrix which may be selected from the group consisting of laminin, fibronectin, vitronectin, proteoglycan, entactin, collagen, collagen I, collagen IV, collagen VIII, heparan sulfate, Matrigel™ (a soluble preparation from Engelbreth-Holm-Swarm (EHS) mouse sarcoma cells), CellStart, a human basement membrane extract, and any combination thereof. Said matrix may comprise Matrigel™ (a soluble preparation from Engelbreth-Holm-Swarm (EHS) mouse sarcoma cells).

The pharmaceutical composition may comprise cells that lack substantial expression of one or more embryonic stem cell markers. Said one or more embryonic stem cell markers may comprise OCT-4, NANOG, Rex-1, alkaline phosphatase, Sox2, TDGF-1, SSEA-3, SSEA-4, TRA-1-60, and/or TRA-1-81.

Said RPE cells may be positive for expression of one or more RPE cell markers. Said one or more RPE cell markers may comprise RPE65, CRALBP, PEDF, Bestrophin, MITF, Otx2, PAX2, PAX6, ZO-1, and/or tyrosinase.

Said RPE cells may be produced by a method comprising maintaining RPE cells as quiescent cells for a time sufficient to attain said average melanin content. Said RPE cells may be produced by a method comprising maintaining RPE cells as quiescent cells for a time sufficient to establish bestrophin expression in at least 50% of said RPE cells.

Said pharmaceutical composition may be substantially free of mouse embryonic feeder cells (MEF) and human embryonic stem cells (hES).

The RPE cells may meet at least one of the criteria recited in Table 1 and/or manufactured in accordance with Good Manufacturing Practices (GMP).

Said cryopreserved retinal pigment epithelial (RPE) cells or photoreceptor progenitors may be provided as a cryopreserved composition.

Said RPE cells may exhibit a rate of phagocytosis of photoreceptor outer segments (POS) that may be at least 50 percent greater than the rate of phagocytosis of POS for an equivalent number of RPE cells from isolated adult eyes, or at least 75, 100, 150 or 200 percent greater than the rate of phagocytosis of POS for an equivalent number of RPE cells from isolated adult eyes; or a rate of phagocytosis of photoreceptor outer segments (POS) that may be at least 20 percent of the total concentration of POS after 24 hours, or at least 25, 30, 25, 40 or 50 percent of the total concentration of POS after 24 hours. Said photoreceptor progenitors may exhibit a rate of phagocytosis of photoreceptor outer segments (POS) that may be at least 50 percent greater than the rate of phagocytosis of POS for an equivalent number of photoreceptor progenitors from isolated adult eyes, or at least 75, 100, 150 or 200 percent greater than the rate of phagocytosis of POS for an equivalent number of photoreceptor progenitors from isolated adult eyes; or a rate of phagocytosis of photoreceptor outer segments (POS) that may be at least 20 percent of the total concentration of POS after 24 hours, or at least 25, 30, 25, 40 or 50 percent of the total concentration of POS after 24 hours. The rate and extent of phagocytosis may depend upon the incubation time and on the maturity of the cells. The rates of binding and internalization of POS can be different based on the maturity and pigmentation of the cells. The percentage of cells capable of phagocytosis may be different based on the maturity of the cell cultures.

By labeling the photoreceptor outer segments with a dye which is non-fluorescent or weakly fluorescent at neutral pH but which becomes more fluorescent upon acidification, a more sensitive measurement of internalized POS in RPE cells or photoreceptor progenitors in a phagocytosis assay is possible. Most of the quantitative methods used for phagocytosis assessment (FACS, fluorescence plate reader) do not discriminate between internalized and surface bound fluorescent particles. Additionally, FITC fluorescence is pH-sensitive and is significantly reduced at pH below 6 while the pH of lysosomes and phagosomes fused with lysosomes is below 5. Thus fluorescence of FITC-labeled OS in some instances is not representative of the actual amount of internalized OS. According to its manufacturer (Life Technologies, Molecular Probes), pH-sensitive rhodamine-based pHrodo® Red dye is non-fluorescent at neutral pH, that upon acidification turns bright red. The dye is both fluorogenic and pH-sensitive, and it can therefore be used as a specific sensor of phagocytic events whereby acidification of the phagosome following phagocytosis is indicated by red fluorescence.

Use of a dye which is non-fluorescent or weakly fluorescent at neutral pH but becomes more fluorescent upon acidification, such as pHrodo® Red and CypHer5E which is also maximally fluorescent in an acidic environment, LysoSensor by Life Technologies dye, to label photoreceptor outer segments is a significant improvement over the prior art methods and reagents. We used this pH-sensitive rhodamine-based pHrodo® Red dye to label bovine OS to specifically measure the internalized particles.

Figure 1B:
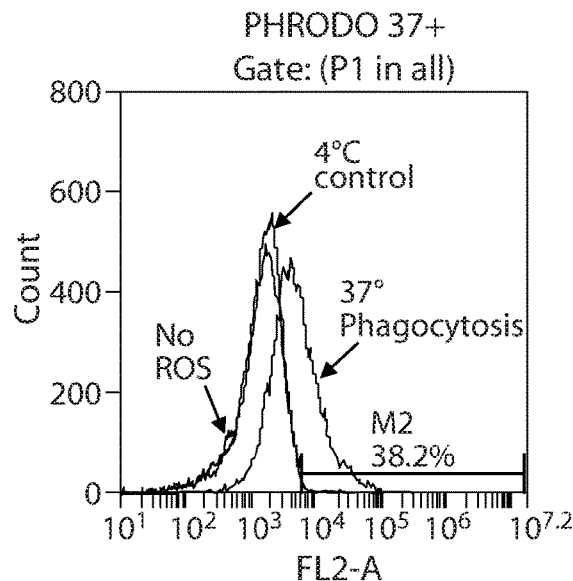
Figure 1C:
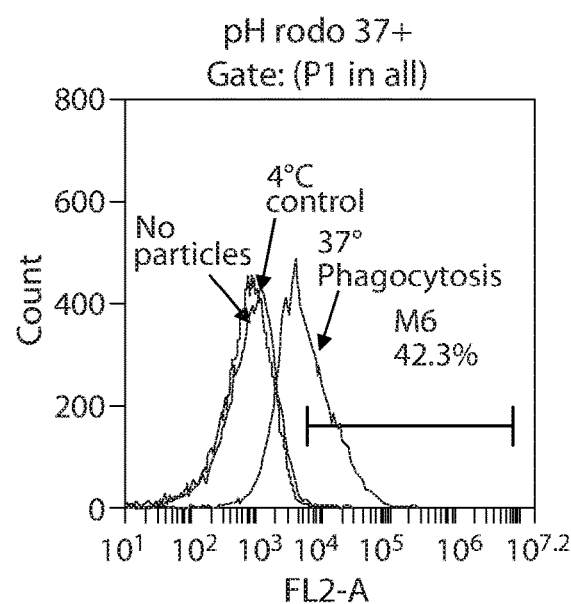
Figure 2A:
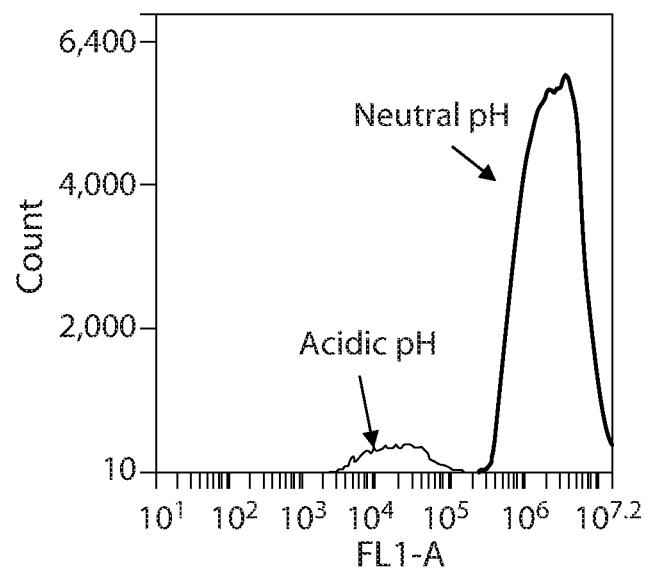
FIGS. 2A-B. pH-dependence of fluorescence of FITC (A) and pHrodo® (B) labeled ROS. Plotted is fluorescence at a neutral pH and at an acidic pH.
Figure 2B:
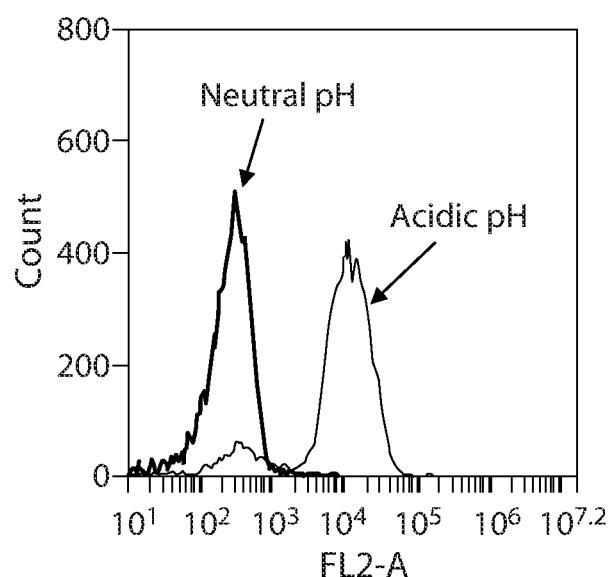
Figure 3A:
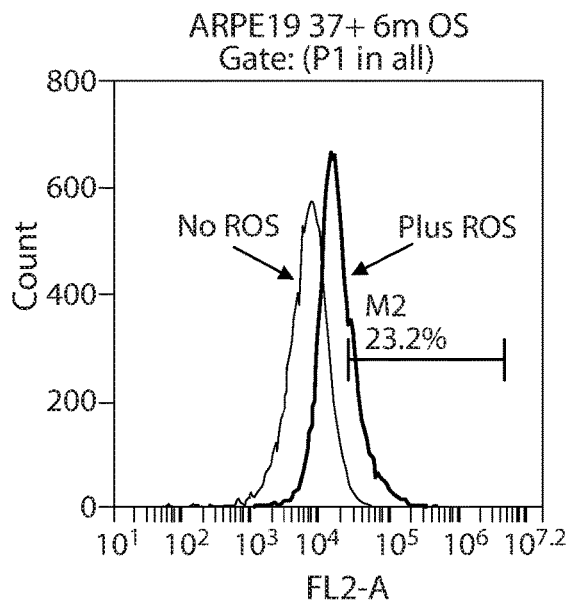
FIGS. 3A-F. FACS analysis of phagocytosis of fluorescently-labeled ROS by ARPE19 cells in monolayer. No dose-dependent response of phagocytosis was observed when different concentrations of fluorescently-labeled ROS were incubated with ARPE-19 for 24 hours in a cell monolayer. (A) ARPE-19 incubated with $6 \times 10^6$ pHrodo® Red-labeled ROS at 37° C. (B) ARPE-19 incubated with $3 \times 10^6$ pHrodo® Red-labeled ROS at 37° C. (C) ARPE-19 incubated with $1.5 \times 10^6$ pHrodo® Red-labeled ROS at 37° C. (D) ARPE-19 incubated with $6 \times 10^6$ pHrodo® Red-labeled ROS at 15° C. (E) ARPE-19 incubated with $3 \times 10^6$ pHrodo® Red-labeled ROS at 15° C. (F) ARPE-19 incubated with $1.5 \times 10^6$ pHrodo® Red-labeled ROS at 15° C. In each, plots for cells incubated with no ROS and for cells incubated with ROS are shown.
Figure 3B:
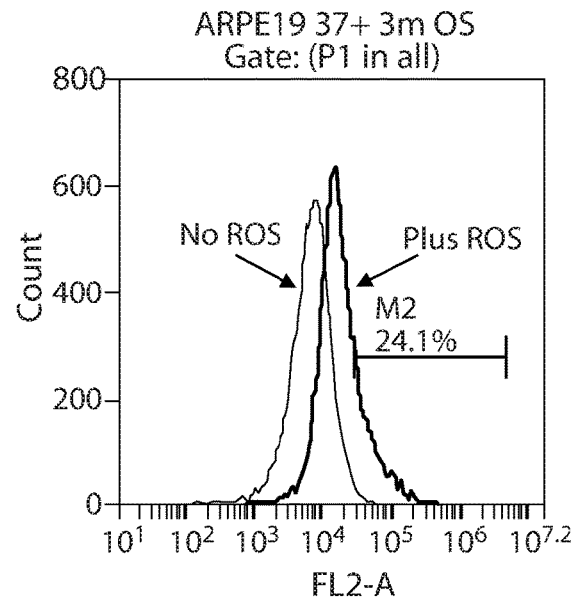
Figure 3C:
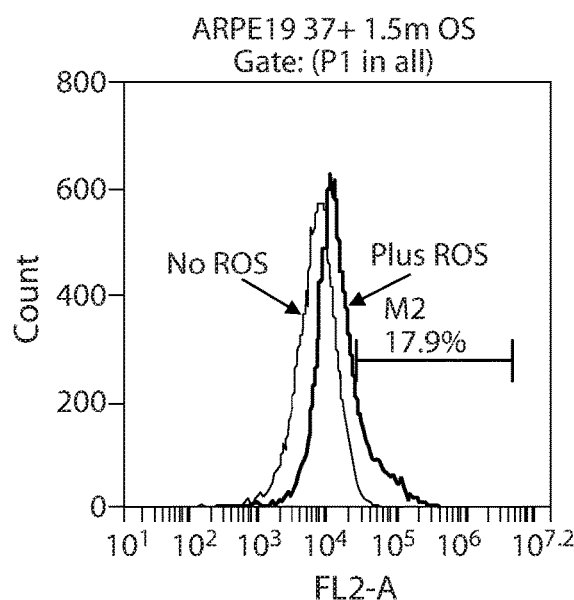
Figure 3D:
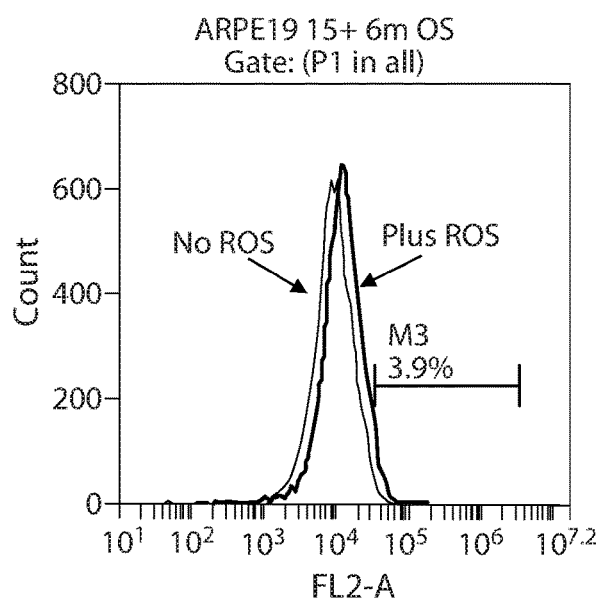
Figure 3E:
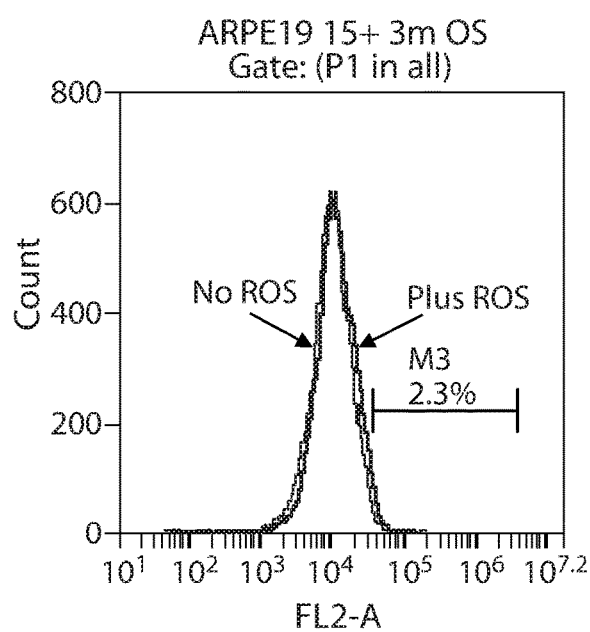
Figure 3F:
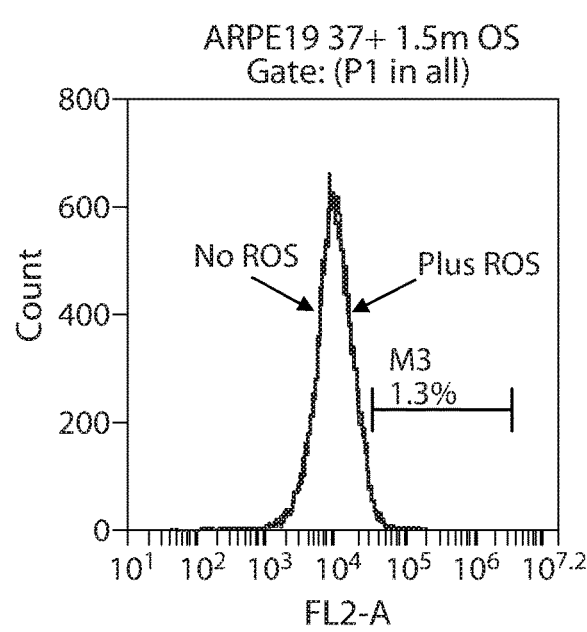
Figure 4A:
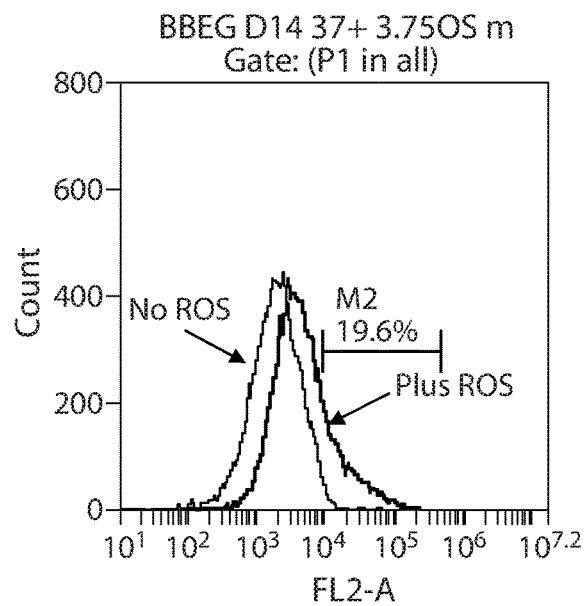
FIGS. 4A-F. FACS analysis of phagocytosis of fluorescently-labeled ROS by hESC-derived RPE cells. No dose-dependent response of phagocytosis was observed when different concentrations of fluorescently-labeled ROS were incubated with RPE for 24 hours at 37° C. in a cell monolayer. Pulse sonication of fluorescently-labeled ROS during reconstitution increased phagocytosis by approximately 10%. (A) RPE cells incubated with $3.75 \times 10^6$ pHrodo® Red-labeled. ROS reconstituted without sonication. (B) RPE cells incubated with $5 \times 10^6$ pHrodo® Red-labeled ROS reconstituted without sonication. (C) RPE cells incubated with $7.5 \times 10^6$ pHrodo® Red-labeled ROS reconstituted without sonication. (D) RPE cells incubated with $10 \times 10^6$ pHrodo® Red-labeled ROS reconstituted without sonication. (E) RPE cells incubated with $10 \times 10^6$ pHrodo® Red-labeled ROS reconstituted with sonication. (F) RPE cells incubated with $13.5 \times 10^6$ pHrodo® Red-labeled ROS reconstituted with sonication.
Figure 4B:
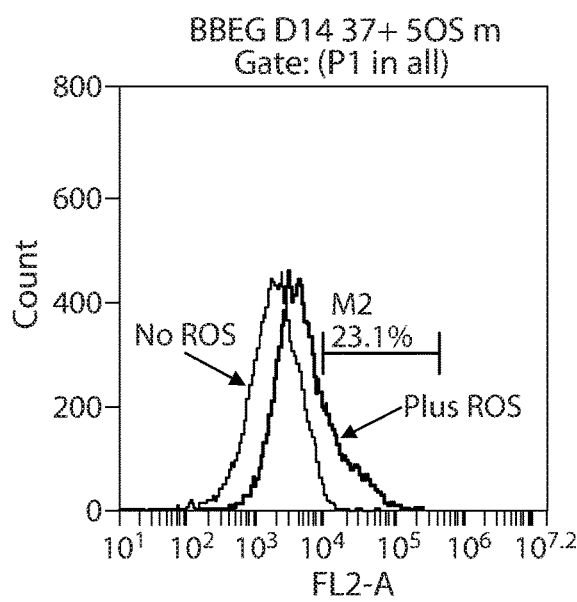
Figure 4C:
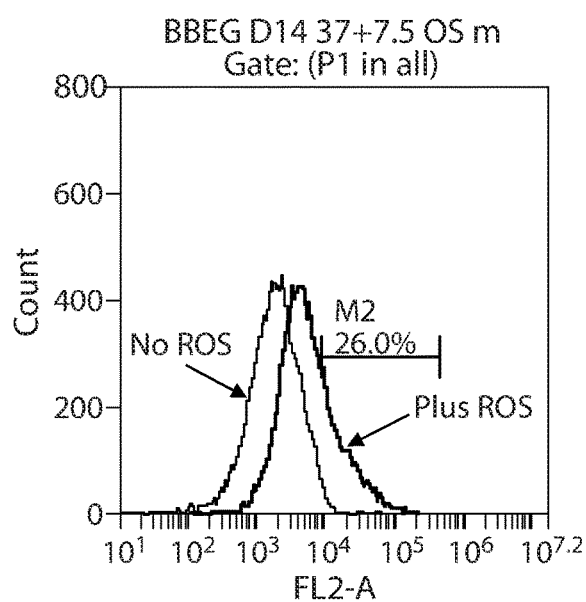
Figure 4D:
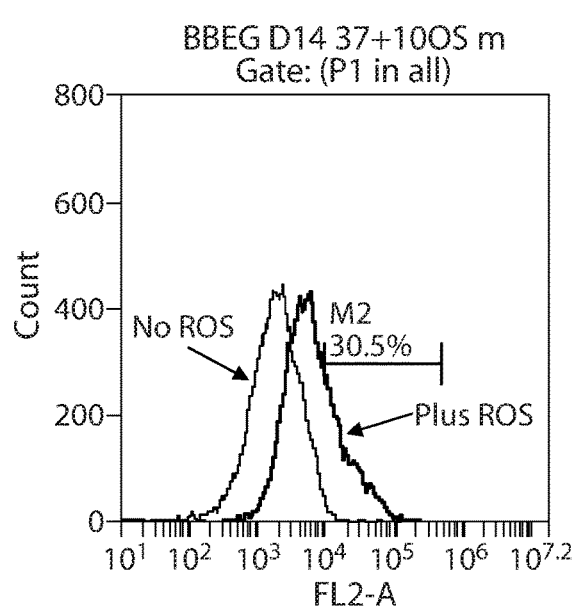
Figure 4E:
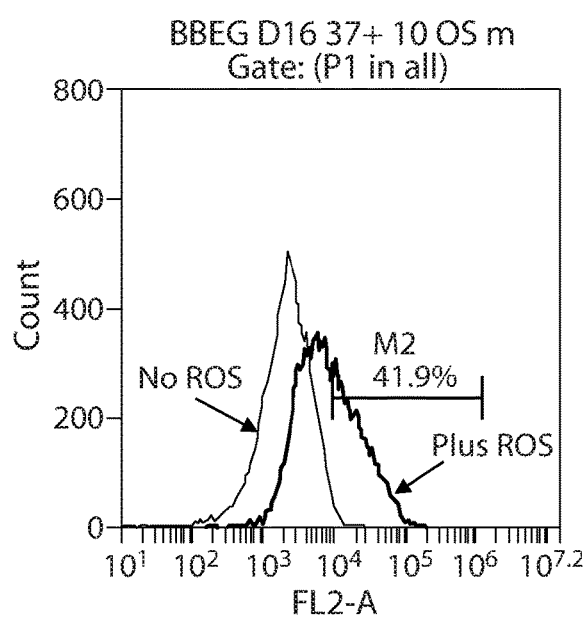
Figure 4F:
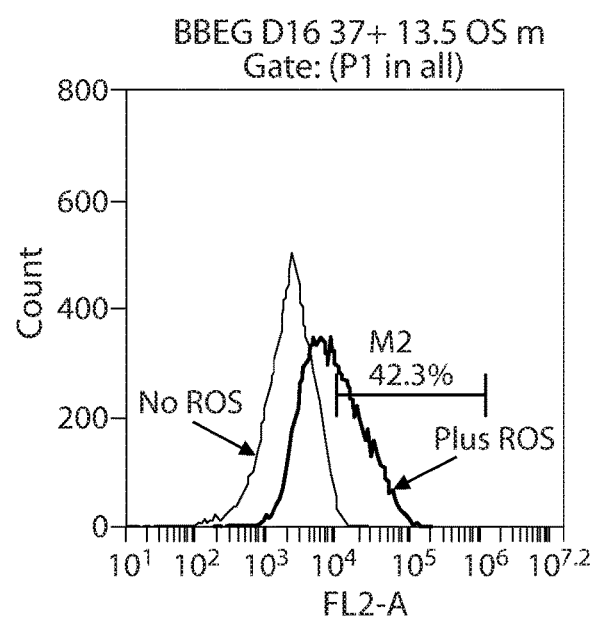

When comparing FITC labeled photoreceptor outer segments, pHrodo®-BioParticles and pHrodo®-labeled photoreceptor outer segments, all showed significant increase in fluorescence (FIGS. 1A-C) in the phagocytosis assay at 37° C. as compared to 4° C. However, quantitative analysis showed that only about half of the RPE cell population at 37° C. in the phagocytosis assay demonstrated increase in fluorescence over 4° C. control when incubated with FITC-labeled particles (FIG. 1A), and in the 4° C. control about half of the RPE cell population also showed significant increase in fluorescence, possibly indicating the presence of bound but non-internalized particles on the cell surface. Such particles on the cell surface could represent both specific and non-specific binding. Additionally, interpretation of the FITC-labeled photoreceptor outer segments FACS data is not very accurate because some of the FITC fluorescence could be lost at low pH (FIG. 2), so once the particles are internalized and phagosomes fuse with lysosomes, at the final low pH (4.5-5.5) some of the FITC fluorescence is lost. Thus the fluorescence as measured includes loss of some signal from internalized particles and additional signal from non-specifically bound particles on the surface. Both pHrodo®-labeled BioParticles and pHrodo®-labeled photoreceptor outer segments did not show any fluorescence increase at 4° C. (FIGS. 1B and 1C) but did show an increase at 37° C., thus allowing specific measurement of only internalized particles fused with lysosomes.

As described herein, pHrodo®-labeled ROS become fluorescent at low pH, so an observed shift in fluorescence indicates particles that are internalized. Use of FITC or other non-pH-sensitive dye-labeled ROS tends to show non-specifically bound particles on the cell surface, specifically bound but not internalized POS, and/or POS that is internalized but not fused with lysosomes. Labeling photoreceptor outer segments with pHrodo® or another pH-sensitive dye, instead of conventionally used FITC, which fluorescence has an inverse correlation with the acidity, or using pHrodo®-labeled POS in combination with other pH-sensitive and/or non-sensitive dye is an improvement in accuracy of the phagocytosis assay as it allows for the measurement of phagocytosis of the physiologically relevant target and allows for the dissection of the mechanisms of phagocytosis.

In some embodiments, the POS are fragmented prior to use with the cells of interest. POS may be fragmented using for example sonication, or shearing, or other methods in the art. It has been found, in some instances, that the fragmented POS result in higher phagocytosis readings from cells. This may be helpful in distinguishing positive activity from control activity.

The phagocytosis assays may be carried out using single cell suspension of cells or they may be carried out using a monolayer of cells. Thus, the cells may be provided as cell suspensions or they may be provided as a monolayer, including a cultured monolayer. This latter embodiment is useful, particularly if the cells grow normally as a monolayer, as it allows the phagocytosis activity of the cells to be determined as such cells would normally exist. The cells may be incubated with the labeled POS as an adherent layer, such as a monolayer, and then may enzyme digested (e.g., trypsin digested) in order to render them a single cell population which can then be analyzed using for example flow cytometry.

In some embodiments, the cells are incubated with POS at a temperature of at or above 17° C., or at or above 18° C., or at or above 19° C. or at or above 20° C. The upper limit of the temperature range may be at or below 42° C., at or below 41° C., at or below 40° C., at or below 39° C., at or below 38° C., or at or below 37° C. Test phagocytosis activity may be measured at these temperatures. The cells may be provided as a monolayer, including a cultured monolayer.

In some embodiments, the test cells or test cell population is incubated with POS at a temperature ranging from 17-40° C., or from 20-40° C., or from 25-40° C., or from 30-40° C., or from 35-40° C., or at a temperature of about 37° C. The negative control may correspond to cells incubated with POS at a temperature ranging from about 4-16° C., 5-16° C., 6-16° C., 7-16° C., 8-16° C., 9-16° C., 10-16° C., 11-16° C., or 12-16° C. The negative control may correspond to cells incubated with POS at a temperature ranging from about 4-15° C., 5-15° C., 6-15° C., 7-15° C., 8-15° C., 9-15° C., 10-15° C., 11-15° C., or 12-15° C. The cells may be provided as a monolayer, including a cultured monolayer.

In some instances, the cells have been previously cryopreserved and are thawed and cultured briefly in order to establish a monolayer. Once in the monolayer, the phagocytosis activity of the cells may be tested as described herein.

In some embodiments, the cells may be exposed to unlabeled POS for a period of time, and then exposed to fluorescently labeled POS to measure phagocytosis for the latter POS. In this way, the cells may be primed prior to the introduction of the labeled POS.

Definitions

In order that the invention herein described may be fully understood, the following detailed description is set forth. Various embodiments of the invention are described in detail and may be further illustrated by the provided examples.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting. The following terms and definitions are provided herein.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Throughout this specification, the word "comprise" or variations such as "comprises" or "comprising" will be understood to imply the inclusion of a stated integer or groups of integers but not the exclusion of any other integer or group of integers.

"Embryonic stem cells" (ES cells), as used herein, refers broadly to cells derived from the inner cell mass of blastocysts or morulae that have been serially passaged as cell lines. The ES cells may be derived from fertilization of an egg cell with sperm or DNA, nuclear transfer, parthenogenesis, or by means to generate ES cells with homozygosity in the HLA region. ES cells may also refer to cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Embryonic stem cells, regardless of their source or the particular method used to produce them, can be identified based on the: (i) ability to differentiate into cells of all three germ layers, (ii) expression of at least Oct-4 and alkaline phosphatase, and (iii) ability to produce teratomas when transplanted into immunocompromised animals. The term also includes cells isolated from one or more blastomeres of an embryo, preferably without destroying the remainder of the embryo (see, e.g., Chung et al., Cell Stem Cell. 2008 Feb. 7; 2(2):113-7; U.S. PGPub No. 20060206953; U.S. PGPub No. 2008/0057041, each of which is hereby incorporated by reference in its entirety). The term also includes cells produced by somatic cell nuclear transfer, even when non-embryonic cells are used in the process. ES cells may be derived from fertilization of an egg cell with sperm or DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Human embryonic stem cells of the present disclosure may include, but are not limited to, MA01, MA09, ACT-4, No. 3, H1, H7, H9, H14 and ACT30 embryonic stem cells. In certain embodiments, human ES cells used to produce RPE cells are derived and maintained in accordance with GMP standards.

"Macular degeneration," as used herein, refers broadly to diseases characterized by a progressive loss of central vision associated with abnormalities of Bruch's membrane, the neural retina, and the retinal pigment epithelium. Macular degeneration diseases include but are not limited to age-related macular degeneration, North Carolina macular dystrophy, Sorsby's fundus dystrophy, Stargardt's disease, pattern dystrophy, Best disease, malattia leventinese, Doyne's honeycomb choroiditis, dominant drusen, and radial drusen.

"Pluripotent stem cell," as used herein, refers broadly to a cell capable of prolonged or virtually indefinite proliferation in vitro while retaining their undifferentiated state, exhibiting a stable (preferably normal) karyotype, and having the capacity to differentiate into all three germ layers (i.e., ectoderm, mesoderm and endoderm) under the appropriate conditions.

RPE cell," "differentiated RPE cell," "ES derived RPE cell," and as used herein, may be used interchangeably throughout to refer broadly to an RPE cell differentiated from a pluripotent stem cell, e.g., using a methods disclosed herein. The term is used generically to refer to differentiated RPE cells, regardless of the level of maturity of the cells, and thus may encompass RPE cells of various levels of maturity. RPE cells can be visually recognized by their cobblestone morphology and the initial appearance of pigment. RPE cells can also be identified molecularly based on substantial lack of expression of embryonic stem cell markers such as Oct-4 and NANOG, as well as based on the expression of RPE markers such as RPE 65, PEDF, CRALBP, and bestrophin. For example, a cell may be counted as positive for a given marker if the expected staining pattern is observed, e.g., PAX6 localized in the nuclei, Bestrophin localized in the plasma membrane in a polygonal pattern (showing localized Bestrophin staining in sharp lines at the cell's periphery), ZO-1 staining present in tight junctions outlining the cells in a polygonal pattern, and MITF staining detected confined to the nucleus. Unless otherwise specified, RPE cells, as used herein, refers to RPE cells differentiated in vitro from pluripotent stem cells.

"Mature RPE cell" and "mature differentiated RPE cell," as used herein, may be used interchangeably throughout to refer broadly to changes that occur following initial differentiating of RPE cells. Specifically, although RPE cells can be recognized, in part, based on initial appearance of pigment, after differentiation mature RPE cells can be recognized based on enhanced pigmentation.

"Pigmented," as used herein refers broadly to any level of pigmentation, for example, the pigmentation that initial occurs when RPE cells differentiate from ES cells. Pigmentation may vary with cell density and the maturity of the differentiated RPE cells. The pigmentation of a RPE cell may be the same as an average RPE cell after terminal differentiation of the RPE cell. The pigmentation of a RPE cell may be more pigmented than the average RPE cell after terminal differentiation of the RPE cell. The pigmentation of a RPE cell may be less pigmented than the average RPE cell after terminal differentiation.

"Photoreceptor progenitor" refers to cells of the neural retina, which may be differentiated from embryonic stem cells or induced pluripotent stem cells and that expresses the marker PAX6 while not expressing the marker CHX10 (i.e. CHX10(−)). These cells transiently express CHX10 at retinal neural progenitor stage, but the CHX10 expression is turned off when cells differentiate into the photoreceptor progenitor stage. Other markers expressed by the photoreceptor progenitors may include: Pax6, Nr2e3, Trβ2, Mash1, RORβ, and NRL. Also, "photoreceptor" may refer to post-mitotic cells differentiated from embryonic stem cells or induced pluripotent stem cells and that expresses the cell marker rhodopsin or any of the three cone opsins, and optionally express the rod or cone cGMP phosphodiesterase. The photoreceptors may also express the marker recoverin, which is found in photoreceptors. The photoreceptors may be rod and/or cone photoreceptors.

Cell Markers: Exemplary cell markers that may be assessed for expression include the following: PAX6, RX1, SIX3, SIX6, LHX2, TBX3, SOX2, CHX10, Nestin, TRβ2, NR2E3, NRL, MASH1, RORβ, Recoverin, Opsin, Rhodopsin, rod and cone cGMP Phosphodiesterase, which may be assessed at the protein and/or mRNA (see Fischer A J, Reh T A, Dev Neurosci. 2001; 23(4-5):268-76; Baumer et al., Development. 2003 July; 130(13):2903-15, Swaroop et al., Nat Rev Neurosci. 2010 August; 11(8):563-76, Agathocleous and Harris, Annu. Rev. Cell Dev. Biol. 2009. 25:45-69, each of which is hereby incorporated by reference in its entirety). Said marker identifiers are generally used as in the literature and in the art, particular in the fields of art in related to the contexts in which those gene identifiers are recited herein, which may include literature related to photoreceptors, rods, cones, photoreceptor differentiation, photoreceptor progenitors, neural differentiation, neural stem cells, pluripotent stem cells, and other fields as indicated by context. Additionally, the markers are generally human, e.g., except where the context indicates otherwise. The cell markers can be identified using conventional immunocytochemical methods or conventional PCR methods which techniques are well known to those of ordinary skill in the art.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," "treat" or "treatment", as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms (e.g., blindness, retinal deterioration.) Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms (e.g., retinal degeneration, loss of vision.) Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., blindness, retinal degeneration).

The RPE or photoreceptor progenitor cells of the preparation may have a rate of phagocytosis of photoreceptor outer segments (POS) that is at least 50 percent greater than the rate of phagocytosis of POS for an equivalent number of RPE cells from isolated adult eyes (i.e., human adult patients from the age of 25-80, more preferably from adults from the age of 50-80), and more preferably at least 75, 100, 150 or even 200 percent greater. The photoreceptor progenitors of the preparation may have a rate of phagocytosis of photoreceptor outer segments (POS) that is at least 50 percent greater than the rate of phagocytosis of POS for an equivalent number of photoreceptor progenitor cells isolated from adult eyes (i.e., human adult patients from the age of 25-80, more preferably adults from the age of 50-80), and more preferably at least 75, 100, 150 or even 200 percent greater.

The RPE or photoreceptor progenitor cells of the preparation may have a rate of phagocytosis of photoreceptor outer segments (POS) that is at least 20 percent of the total concentration of POS after 24 hours, and more preferably at least 25, 30, 25, 40 or even 50 percent of the total concentration of POS after 24 hours, POS phagocytosis can be measured, as one illustrative and non-limiting example, using the protocols described in Bergmann et al. FASEB Journal March 2004 vol. 18 pages 562-564, with the variation of the non-FITC labeled POS described herein.

The RPE or photoreceptor progenitor cell populations may include differentiated RPE cells of varying levels of maturity, or may be substantially pure with respect to differentiated RPE cells of a particular level of maturity. The RPE cells may be a substantially purified preparation comprising RPE cells of varying levels of maturity/pigmentation Cryopreserved Preparations of RPE Cells The RPE cells or photoreceptor progenitors may be stored by any appropriate method known in the art (e.g., cryogenically frozen) and may be frozen at any temperature appropriate for storage of the cells. Prior to use of these cells, they may be tested in an assay of the invention to determine phagocytosis activity and/or potency of the cells.

The RPE cells or photoreceptor progenitor cells that show potency in the phagocytosis assay of the invention may be used for treating retinal degeneration diseases due to retinal detachment, retinal dysplasia, Angioid streaks, Myopic Macular Degeneration, or retinal atrophy or associated with a number of vision-altering ailments that result in photoreceptor damage and blindness, such as, choroideremia, diabetic retinopathy, macular degeneration (e.g., age-related macular degeneration), retinitis pigmentosa, and Stargardt's Disease (fundus flavimaculatus).

The RPE or photoreceptor progenitor cells provided herein may be human RPE or photoreceptor progenitor cells. Note, however, that the human cells may be used in human patients, as well as in animal models or animal patients. For example, the human cells may be tested in mouse, rat, cat, dog, or non-human primate models of retinal degeneration. Additionally, the human cells may be used therapeutically to treat animals in need thereof, such as in veterinary medicine.

Screening Assays

The disclosure provides a method for identifying agents that modulate RPE cell or photoreceptor progenitor phagocytic activity.

EXAMPLES

The invention now being generally described, it will be more readily understood by reference to the following examples, which are included merely for purposes of illustration of certain aspects and embodiments of the present invention, and are not intended to limit the invention.

RPE cells were derived from human embryonic stem cells (hESC) as previously described (Klimanskaya et al, 2004) and were used at passages 2 through 5 after isolation from pigmented cluster differentiation culture. Cells were cultured in EGM-2 medium (Lonza) until they reached confluence and in RPE maintenance medium (Klimanskaya et al, 2004) after that Cells used in experiments had established a differentiated RPE phenotype characterized by hexagonal morphology, various levels of brown pigment, cuboidal cell appearance, polarization and tight junctions. Alternatively, cells were used in experiments before they fully matured but still after they became confluent.

Bovine Rod Outer Segments (catalog #98740) procured from: InVision Bioresources. FITC isomer (catalog #F1906) I procured from Life Technologies. pHrodo® Red Phagocytosis Particle Labeling Kit (catalog #A10026) procured from Life Technologies.

Labeling POS with FITC

Resuspended 1 vial of 10 mg FITC Isomer I to 2 mg/mL in 0.1 M Sodium Carbonate Buffer, 9.5. Spun down at 3000 g for 10 minutes to remove undiluted particles and only used supernatant for labeling bovine ROS. Thawed 25 bovine eyeballs worth of ROS and resuspended in 5 mL wash buffer (10% sucrose in 20 mM phosphate buffer with 5 mM taurine, pH 7.2). Added 1.5 mL of 2 mg/mL FITC supernatant to the resuspended ROS and let them incubate in dark with rocking for 1 hr at RT. After incubation, spun ROS-FITC segments down at 3000 g and resuspended in 10 mL wash buffer. Repeated this washing step a total of 2 times. After washing, resuspended in 10 mL 2.5% sucrose in DMEM (Gibco #11960) and spun down again at 3000 g for 10 minutes. Finally, resuspended cells in 10 mL 2.5% sucrose in DMEM, counted ROS-FITC particles using a hemacytometer, adjusted concentration to $1*10^8$ particles/mL in 2.5% sucrose in DMEM, and froze down particles −80° C.

Labeling POS with pHrodo®

Resuspended 25 bovine eyes worth of ROS in 4.165 mL 0.1 M Sodium Bicarbonate buffer from pHrodo® Red phagocytosis Particle Labeling kit. Aliquoted ROS out into 4 750 μL aliquots in microcentrifuge tubes. Centrifuged tubes at 10000 RPM for 1 minute, and then resuspended in 750 μL 0.1 M Sodium Bicarbonate buffer again. Resuspended pHrodo® dye to a final concentration of 10 mM in DMSO. Added pHrodo® dye to ROS in sodium bicarbonate buffer to a final concentration of 0.5 mM, and incubated in the dark for 45 minutes. After 45 minutes, added 500 μL "Component C" (from kit) and centrifuged at 10000 RPM for 1 minute. Aspirated supernatant and resuspended in 1 mL 100% methanol. Vortexed tubes for 30 seconds and spun down at 10000 RPM for 1 minute. Aspirated methanol and resuspended in 1 mL "Component C" (wash buffer from kit) and centrifuged again at 10000 RPM for 1 minute. Repeated this wash step a total of 2 times. Resuspended all particles in a total of 20 mL "Buffer B" (from kit). Spun ROS-pHrodo® down at 3000 RPM for 10 minutes, resuspended ROS-pHrodo® in 2.5% sucrose in DMEM, adjusted concentration to $1*10^8$ particles/mL in 2.5% sucrose in DMEM, and froze down particles at −80° C.

RPE cells were incubated with either pHrodo®-conjugated BioParticles or with bovine outer segments labeled with either FITC or pHrodo® for various time from 2 to 24 h at 37° C. After that the cells were washed, harvested by trypsin/dissociation buffer, 1:1, centrifuged and analyzed by flow cytometry. As a negative control, cells were incubated for the same length of time at 4° C.

Additionally, interpretation of the FITC-labeled ROS FACS data is not very accurate because some of the FITC fluorescence could be lost at low pH (FIGS. 2A and B), so once the particles are internalized and phagosomes fuse with lysosomes, the final low pH (4.5-5.5) some of the FITC fluorescence is lost. Thus the fluorescence as measured includes loss of some signal from internalized particles and additional signal from non-specifically bound particles on the surface.

pHrodo® is pH-sensitive fluorescent dye, and both pHrodo®-labeled BioParticles and ROS did not show any fluorescence increase at 4° C. (FIGS. 1B and 1C) thus allowing to specifically measure only internalized particles fused with lysosomes.

Labeling ROS with pHrodo® is an improvement in accuracy of the phagocytosis assay and can be used instead of or complementary to FITC-labeled. ROS to dissect the complex mechanisms of phagocytosis.

Labeling with pHrodo® *E. coli* Fluorescent Bioparticles

Phagocytosis is assessed by a FACS-based assay using pHrodo® *E. coli* fluorescent bioparticles (Invitrogen) which fluoresce when internalized in the reduced pH environment of intracellular phagosomes. Bioparticles were prepared according to the manufacturer's instructions. Confluent RPE were incubated with 50-200 µL bioparticles per one well of a 4-well plate in $CO_2$-independent medium (Invitrogen) for 16-20 hours at 37° C. Negative control plates were incubated at 4° C. Cells were examined under the microscope, harvested by trypsin and analyzed by FACS counting 10,000 events on a C6 Flow Cytometer.

TABLE 1

RPE Cell Characterization and Safety Testing

| Test | Specification | Test lot |
|---|---|---|
| Sterility | Negative | Negative |
| Mycoplasma | Negative | Negative |
| Cell density | 1-2 million viable cells/mL (post dilution) | $2 \times 10^6$ viable cells/mL |
| Cell viability | Final harvest: >85% | 99% |
|  | Post-thaw: >70% | 95% |
| Morphology | Confluent, cobblestone epithelium, medium pigmentation | Pass |
| Karyotype | 46, XX, normal | 46, XX, normal |
| DNA fingerprinting | Conforms with hESC MCB | Conforms |
| hRPE mRNA for: BEST-1 | Up-regulated by a minimum of 1 $\log_{10}$ compared to hESC | RPE-6   1.32 |
| RPE-65 |  | PAX6   2.80 |
| PAX6 |  | MITF   2.89 |
| MITF |  | BEST-1   3.81 |
|  | Down-regulated compared to hESC ($\log_{10}$): |  |
| hESC mRNA for: OCT-4 | OCT-4 ≤−2.13 | OCT-4   −3.18 |
| NANOG | NANOG ≤−1.95 | NANOG   −2.49 |
| SOX-2 | SOX-2 ≤−0.63 | SOX-2   −2.07 |
| Maturity by bestrophin staining | >70% staining | 71% |
| Purity by immunostaining | >95% PAX6 and/or MITF | 100% |
|  | >95% PAX6 and/or bestrophin | 100% |
|  | >95% ZO-1 | 100% |
| hESC protein markers | <2 cells staining with OCT-4 and AP in 9 million cells examined | 0 |
| Residual murine DNA | Negative | Negative |
| Murine viruses by MAP | Negative | Negative |
| Retroviruses by *Mus dunni* co-cultivation | Negative | Negative |
| Ecotropic murine viruses | Negative | Negative |
| Endotoxin | <0.50 EU/mL | 0.312 EU/mL |
| Potency by phagocytosis | Positive | Positive |

Phagocytosis of pHrodo® Red-Labeled ROS by RPE Cells.

hESC-derived RPE and ARPE-19 cells were cultured in RPE Growth Medium (RPE-GM) consisting of Endothelial Cell Growth Medium (Lonza, cat #CC-3162, CC-3156).

For the phagocytosis assay, RPE cells were seeded in 96-well culture plates (Becton-Dickinson) at a density of $5 \times 10^5$ cells/cm² and maintained in a humidified incubator at 37° C. with 5% $CO_2$. For optimal assay readings, RPE cells were cultured for 3-5 days in RPE-GM prior to evaluation of phagocytosis capability. If cells were cultured longer than 5 days, RPE-GM was switched to RPE Maintenance Medium (RPE-MM) consisting of DMEM supplemented with 10% Fetal Bovine Serum, GlutaMax and Normocin. The medium was changed every 2-3 days to provide sufficient nutrition.

For the determination of phagocytotic activities of RPE cells, pH-sensitive Rhodamine-based pHrodo® Red-labeled Rod Outer Segments (ROS) (InVision Bioresources, cat. #98740) were used. ROS labeling with pHrodo® Red Microscale Labeling Kit (Thermo: Fisher Scientific, cat. #P35363) was previously described. Each well of confluent RPE cells was inoculated with 0.1 mL DMEM medium containing 10% FBS and Normocin and 0.1 mL labeled ROS, reconstituted in DMEM supplemented with 10% FBS and Normocin. To evaluate optimal phagocytotic capability of RPE cells, different ROS concentrations of $1.5 \times 10^6$, $3 \times 10^6$, $3.75 \times 10^6$, $5 \times 10^6$, $6 \times 10^6$, $7.5 \times 10^6$, $10 \times 10^6$ and $13.5 \times 10^6$ ROS/well of a 96-well plate were tested. To decrease ROS aggregates and increase phagocytosis efficiency, a direct pulse-sonication step was introduced during reconstitution of Rod Outer Segments. RPE cells and ROS were incubated for 20 to 28 hours at 37° C. for the test samples and 12-15° C. for the negative control in an atmosphere of 5% $CO_2$ and 95% air. Next day, after 20 to 28 hours incubation of ROS with RPE cell monolayer, culture medium was aspirated and each well was washed 3× with 0.2 mL Ca/Mg-free PBS (Gibco/Invitrogen #14190-250). 0.2 mL of 0.25% Trypsin/EDTA (Sigma, cat. #T4049) plus Cell Dissociation Buffer (Gibco/Invitrogen, cat. #13151) was added to each well in a 1:1 ratio and incubated at room temperature until a single cell suspension was visible (10-20 minutes), Cell suspension of each sample was transferred to appropriately labeled round-bottom, polystyrene tube containing 2 mL DMEM plus 10% FBS to neutralize reaction and centrifuged at 160 g for 5 minutes. Supernatant was decanted by leaving ~0.2-0.25 mL liquid behind. Sample tubes were vortexed and ROS uptake by RPE cells was evaluated using BD Accuri C6 Flow Cytometer as previously described.

To further increase phagocytotic capability, naïve RPE cells in monolayer can be rendered "competent" by exposure to unlabeled ROS for defined periods of time with or without recovery steps prior to performing phagocytosis of pHrodo® Red-labeled ROS following the above described procedure.

REFERENCES

Schwartz S D, Hubschman J P, Heilwell G, Franco-Cardenas V, Pan C K, Ostrick R M, Mickunas E, Gay R, Klimanskaya I, Lanza R. Embryonic stem cell trials for macular degeneration: a preliminary report. Lancet. 2012 Feb. 25; 379(9817):713-20. doi: 10.1016/S0140-6736(12) 60028-2. Epub 2012 Jan. 24. PubMed PMID: 22281388.

Klimanskaya I. Retinal pigment epithelium. Methods Enzymol. 2006; 418:169-94. PubMed PMID: 17141036.

Lund R D, Wang S, Klimanskaya I, Holmes T, Ramos-Kelsey R, Lu B, Girman S, Bischoff N, Sauvé Y, Lanza R. Human embryonic stem cell-derived cells rescue visual function in dystrophic RCS rats, Cloning Stem Cells. 2006 Fall; 8(3):189-99. PubMed PMID: 17009895.

Klimanskaya I, Hipp J, Rezai K A, West M, A ala A, Lanza R. Derivation and comparative assessment of retinal pigment epithelium from human embryonic stem cells using transcriptomics. Cloning Stem Cells. 2004; 6(3):217-45. PubMed PMID: 15671670.

Mao Y, Finnemann S C. Analysis of photoreceptor outer segment phagocytosis by RPE cells in culture. Methods Mol Biol. 2013; 935:285-95. doi: 10.1007/978-1-62703-080-9_20. PubMed PMID: 23150376; PubMed Central PMCID: PMC3590840.

Finnemann S C, Bonilha V L, Marmorstein A D, Rodriguez-Boulan E. Phagocytosis of rod outer segments by retinal pigment epithelial cells requires alpha(v)beta5 integrin for binding but not for internalization. Proc Natl Acad Sci USA. 1997 Nov. 25; 94(24):12932-7. PubMed PMID: 9371778; PubMed Central PMCID: PMC24241.

Miksa M, Komura H, Wu R, Shah K G, Wang P. A novel method to determine the engulfment of apoptotic cells by macrophages using pHrodo succinimidyl ester. J Immunol Methods. 2009 Mar. 15; 342(1-2):71-7. doi: 10.1016/j.jim.2008.11.019. Epub 2009 Jan. 9. PubMed PMID: 19135446; PubMed Central PMCID: PMC2675277.

Lu B, Malcuit C, Wang S, et al. Long-term safety and function of RPE from human embryonic stem cells in preclinical models of macular degeneration. Stem Cells 2009; 21, 2125-2135.

Sparrow J R, Hicks D, Hamel C P. The retinal pigment epithelium in health and disease. Curr Mol Med 2010; 10, 802-823.

Strauss O. The retinal pigment epithelium in visual function. Physiol Rev 2005; 85, 845-881.

What is claimed is:

1. A method for assessing phagocytosis activity comprising
incubating test cells with photoreceptor outer segments (POS) for a time and temperature sufficient for the cells to phagocytose the POS, wherein the POS are labeled with a fluorescent label that fluoresces more at an acidic pH than at a higher pH, and
detecting fluorescence intensity of the test cells after incubation, wherein an increase in fluorescence intensity compared to a control indicates phagocytosis of the POS by the cells,
wherein the cells are incubated with the POS at a temperature ranging from 25-40° C., or 34-40° C., or at about 37° C., and
wherein the control is control cells incubated with the POS at a temperature ranging from 10-16° C. or 12-15° C.

2. The method of claim 1, wherein the test cells are incubated with the POS at a temperature ranging from 34-40° C. or at about 37° C.

3. The method of claim 1, wherein the test and control cells are incubated with the POS for about 16-20 hours.

4. The method of claim 1, wherein the test and control cells are retinal pigment epithelium (RPE) cells.

5. The method of claim 1, wherein the test and control cells are photoreceptor progenitor cells.

6. The method of claim 1, wherein the POS are labeled with pHrodo® Red dye.

7. The method of claim 1, wherein the control is control cells incubated with the POS at a temperature ranging from 12-15° C.

8. The method of claim 1, wherein the POS are labeled with a fluorescent label having an increased fluorescence signal when internalized by phagocytosis into a low pH compartment in a cell relative to the fluorescence signal when present extracellularly, and
wherein the method comprises detecting an increased fluorescence, if any, in the test cells after incubation with the labeled POS relative to control, and quantifying the phagocytosis activity of the test cells therefrom.

9. The method of claim 1, wherein the test and control cells are produced by in vitro differentiation of pluripotent stem cells.

10. The method of claim 1, wherein the cells are human RPE cells or human photoreceptor progenitor cells.

11. The method of claim 1, wherein the POS are fragmented POS or sonicated POS.

12. A method for measuring phagocytosis activity comprising
(1) measuring a test fluorescence in a first aliquot of the cells incubated with pHrodo® Red labeled photoreceptor outer segments (POS) and/or with pHrodo® Red *E. coli* BioParticles, at a temperature ranging from 25-40° C., or 34-40° C., or about 37° C. to obtain a test fluorescence, and (2) measuring a control fluorescence in a second aliquot of the cells incubated with pHrodo® Red labeled photoreceptor outer segments (POS) and/or with pHrodo® Red *E. coli* BioParticles, at a temperature ranging from 10-16° C. or 12-15° C. to obtain a control fluorescence, wherein a test fluorescence that is greater than a control fluorescence indicates phagocytosis activity of the cells.

13. The method of claim 12, wherein the first aliquot of cells is incubated at a temperature ranging from 34-40° C., or about 37° C.

14. The method of claim 12, wherein the second aliquot of cells is incubated at a temperature of about 12-15° C.

15. The method of claim 12, wherein the cells are human RPE cells or human photoreceptor progenitor cells.

16. A method for measuring phagocytosis activity comprising
    (1) measuring a test fluorescence in a first aliquot of cells incubated with pHrodo® Red labeled photoreceptor outer segments (POS) and/or pHrodo® Red labeled bacterial fragments, at a temperature ranging from 25-40° C., or 34-40° C., or about 37° C. to obtain a test fluorescence, and
    (2) measuring a control fluorescence in a second aliquot of the cells incubated with pHrodo® Red labeled POS and/or pHrodo® Red labeled bacterial fragments, at a temperature ranging from 10-16° C. or 12-15° C. to obtain a control fluorescence,
    wherein a test fluorescence that is greater than a control fluorescence indicates phagocytosis activity of the cells,
    wherein the cells are human RPE cells or human photoreceptor progenitor cells.

17. The method of claim 16, wherein the first and second aliquot of cells are incubated with pHrodo® Red labeled POS.

18. The method of claim 16, wherein the first and second aliquot of cells are incubated with pHrodo® Red labeled bacterial fragments.

19. The method of claim 18, wherein the pHrodo® Red labeled bacterial fragments are pHrodo® Red labeled *E. coli* BioParticles.

20. The method of claim 19, wherein the first aliquot of cells is incubated at a temperature of about 37° C. and the second aliquot of the cells is incubated at a temperature ranging from 12-15° C.

21. The method of claim 20, wherein the cells are human RPE cells.

22. The method of claim 20, wherein the cells are human photoreceptor progenitor cells.

* * * * *

UNITED STATES PATENT AND TRADEMARK OFFICE
CERTIFICATE OF CORRECTION

| | | |
|---|---|---|
| PATENT NO. | : 11,422,125 B2 | Page 1 of 1 |
| APPLICATION NO. | : 15/560584 | |
| DATED | : August 23, 2022 | |
| INVENTOR(S) | : Klimanskaya et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 485 days.

Signed and Sealed this
Fourteenth Day of January, 2025

Derrick Brent
*Acting Director of the United States Patent and Trademark Office*